United States Patent
Denisenko et al.

(10) Patent No.: US 8,569,363 B2
(45) Date of Patent: *Oct. 29, 2013

(54) ANTIMICROBIAL AND RADIOPROTECTIVE COMPOUNDS

(75) Inventors: Peter Prokofievich Denisenko, St. Petersburg (RU); Nikolay Sergeevich Sapronov, St. Petersburg (RU); Alexander Alexandrovich Tarasenko, St. Petersburg (RU)

(73) Assignee: Biodiem Ltd., Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,054

(22) Filed: Mar. 20, 2012

(65) Prior Publication Data

US 2012/0225935 A1 Sep. 6, 2012

Related U.S. Application Data

(63) Continuation of application No. 12/776,896, filed on May 10, 2010, now Pat. No. 8,158,664, which is a continuation of application No. 11/923,404, filed on Oct. 24, 2007, now Pat. No. 7,825,145, which is a continuation of application No. 10/481,667, filed as application No. PCT/AU02/00783 on Jun. 14, 2002, now abandoned.

(30) Foreign Application Priority Data

Jun. 18, 2001 (RU) .................................. 2001117033

(51) Int. Cl.
*A61K 31/36* (2006.01)
*A61P 31/10* (2006.01)
*A61P 31/04* (2006.01)

(52) U.S. Cl.
USPC ........................................................ 514/466

(58) Field of Classification Search
USPC ........................................................ 514/466
See application file for complete search history.

(56) References Cited

U.S. PATENT DOCUMENTS

| | | | |
|---|---|---|---|
| 4,469,703 A | 9/1984 | Kis-Tamas et al. | |
| 6,329,536 B1 | 12/2001 | Ji et al. | |
| 7,825,145 B2 * | 11/2010 | Denisenko et al. | 514/375 |

FOREIGN PATENT DOCUMENTS

| | | |
|---|---|---|
| DE | 2423317 | 12/1975 |
| DE | 347818 | 1/1992 |
| FR | 2115089 | 11/1970 |
| FR | 2768728 | 3/1999 |
| FR | 2768729 | 3/1999 |
| JP | 33-6995 | 8/1958 |
| JP | 56-86136 | 7/1981 |
| JP | 59-67273 | 4/1984 |
| JP | 62/042923 | 8/1985 |
| JP | 63-22023 | 1/1988 |
| JP | 11-171773 | 6/1999 |
| JP | 2000-501398 | 2/2000 |
| RU | 2145215 C1 | 2/2000 |
| RU | 2148215 | 4/2000 |
| WO | WO 97/30046 | 8/1997 |
| WO | WO 98/25917 | 6/1998 |
| WO | WO 99/16755 | 4/1999 |
| WO | WO 00/12089 | 3/2000 |
| WO | WO 00/15599 | 3/2000 |
| WO | WO 02/09684 A2 | 2/2002 |

OTHER PUBLICATIONS

Schales et al. Journal of the American Chemical Society (1952), vol. 74, pp. 4486-4490.*
American Heritage Stedman's Medical Dictionary excerted on 2013 online: definition of *Micrococcus pyogenes* var. aureus.*
Koremura et al. Takamine Kenkyusho Nenpo (1961), vol. 13, pp. 222-227.*
European Search Report issued in Application No. 02734905.9 dated Feb. 26, 2007.
International Search Report issued in PCT/AU02/00783 dated Aug. 16, 2002.
Russian Search Report issued in RU 2001/117033/14 dated Jun. 18, 2001.
Bakhmutov, et al., Chemical Abstract No. 91:19280, Izv. Akad. Nauk SSSR, Ser. Khim., 3:647-50 (1979).
Burton, H. et al., "Synthesis of Derivatives of 5,6-Dihydroxyindole. Part I. 5,6 Methylenedioxyindole and its 2-Methyl Derivative." Journal of the Chemical Society, Chemical Society, London GB, pp. 78-79 (1949).
Basmadjian et al., Chemical Abstract No. 89:126200, Lloydia, 41(4):375-80 (1978).
Bilich et al., "Anti-Candida Properties of Certain β-Nitrostyrene Derivatives," Kiev Regional Dermato-Venereological Centre (1968).
Blake et al., Chemical Abstract No. 80:26692, J. Chem. Soc., Perkin Transactions, 2(12):1660-3 (1973).

(Continued)

*Primary Examiner* — Yong Chu
(74) *Attorney, Agent, or Firm* — Haynes and Boone, LLP

(57) ABSTRACT

Disclosed is a method of treatment and/or prophylaxis of a microbial infection, employing compounds of formula (I), in which X and Y are either the same of different and selected from a herreroatiom; is a double or single bond depending on the heteroatoms X and Y; $R_1$ to $R_5$ are either the same or different and selected from hydrogen or a non-deleterious substituent; and $R_6$ to $R_7$ are either the same or different and selected from hydrogen and a non-deleterious substituent or one of $R_6$ to $R_7$ are absent when there is a double bond present. Also disclosed are methods for protecting a subject from radiation damage, methods of cancer radiotherapy, and use of the disclosed compounds as an antimicrobial or radioprotective agent.

7 Claims, 2 Drawing Sheets

(56) References Cited

OTHER PUBLICATIONS

Cassels et al., Chemical Abstract No. 97:402, An. Assoc. Quim., Argent, 70(2):283-8 (1982).
Chang et al., Chemical Abstract No. 134:310932, Chin. Chem. Let., 12(1):15-18 (2001).
Clark et al., Chemical Abstract No. 123:179638, J. Chromatogr. Sci., 33(6):328-37 (1995).
Clark et al., Chemical Abstract No. 124:78867, J. Chromatogr. Sci., 34(1):34-42 (1996).
Clark et al., "Analysis of 1-(3-Methoxy-4,5-Methylenedioxyphenyl)-2-Propanamine (MMDA) Derivatives Synthesized From Nutmeg Oil and 3-Methoxy-4,5-Methylenedioxybenzaldehyde," J. Chromatogra Sci., 34:34-42 (1996).
Cleaver et al., Chemical Abstract No. 86:43869, Aust. J. Chem., 29(9):2003-21 (1976).
Cserhati et al., Chemical Abstract No. 108:197839, Chromaographia, 25(2):82-6 (1988).
Dallacker et al., Chemical Abstract No. 71:21793, Monatsh. Chem., 100(2):742-7 (1969).
Dauzonne et al., Chemical Abstract No. 106:119379, Chem. Pharm. Bull., 34(4):1628-33 (1986).
Dawson et al., Chemical Abstract No. 114:246703, Magn. Reson. Chem., 29(2):188-90 (1991).
Dore et al., Chemical Abstract No. 79:132914, Chim. Ther., 8(1):80-4 (1973).
Gardiner et al., Chemical Abstract No. 112:98944, J. Org. Chem., 55(4):1261-6 (1990).
Hellot et al., Chemical Abstract No. 73:3565, Chim. Ther., 5(1):55-64 (1970).
Hull and Knight Chemical Abstract No. 126:293221, J. Chem. Soc., Perkin Transactions I: Organic and Bio-Organic Chemistry, 6:857-63 (1997).
Ji et al., Chemical Abstract No. 132:35317, J. Amer. Chem. Soc., 121(43):10215-6 (1999).
Kametani et al., Chemical Abstract No. 66:28635, Yakugaku Zasshi, 86(10):984-8 (1966).
Knoevenagel and Walter, "Condensation and Aliphatic Nitro Compounds with Aromatic Aldehydes by Organic Bases," Rep. German Chem. Soc., 37 (1904).
Kobayashi et al., Chemical Abstract No. 84:74080, Chem. Pharm. Bull., 23(11), ppLIM, et al., Chemical Abstract No. 116:53080, Biol. Mass Spectrum, 20(11):677-86 (1991); 3036-7 (1975).
Kobayashi et al, Chemical Abstract No. 93:72043, Fukusokan Kagaku Toronkai Koen Yoshishu, 12:196-200 (1979).
Kochetkov et al., Chemical Abstract No. 93:71224, Izv. Akad. Nauk SSSR, Ser. Khim., 3:639-41 (1980).
Kodukulla, Ram Prasad K. et al., "Synthesis, Chemical Transformation and Antimicrobial Activity of a Novel Class of Nitroolefins: 1,3-Diaryl-2Nitroprop-1Enes," Synthetic Communications, 24(6):819-832 (1994).
Koremura, M. et al., "Studies on some relationships between chemical structures and antimicrobal and insecticidal activities in organonitro compounds. X. Chemotherapic activities in phenylnitroalkene derivatives." Takamine Kenkyusho Nenpo 13:222-227 (1961).
Kovacs et al., Chemical Abstract No. 95:219667, Kem. Kozl., 54(2-3):308-12 (1980).
Lim et al., Chemical Abstract No. 116:53080, Biol. Mass Spectrum, 20(11):677-86 (1991).
McNulty et al., Chemical Abstract No. 134:295973, Bioorganic & Medicinal Chem. Let., 11(2):169-72 (2001).
Mitsunobu, Koremura, Journal of the Agricultural Chemical Society of Japan, 36:557-560 (1961).
Mitsunobu, Koremura, "Studies on Some Relationships Between Chemical Structures and Antimicrobial and Insecticidal Activities in Organonitro Compounds," The Annual Report of Takamine Laboratory 13:205-211 and 13:212-215 (1961).
Nichols, D.E. et al., "Steric Effects of Substituents on Phenethylamine Hallucinogens 3,4-(Methylenedioxy) Amphetamine Analogues Alkylated on the Dioxole Ring," Journal of Medicinal Chemistry, 22(10):1264-1267 (1979).
Nichols and Kostuba, Chemical Abstract No. 91:151070, J. Med. Chem., 22(10):1264-7 (1979).
Nichols and Kostuba, "Steric Effects of Substituents on Phenethylamine Hallucinogens, 3,4-(Methylenedioxy) Amphetamine Analogues Alkylated on the Dioxole Ring," J. Med. Chem., 22(10):1264-67 (1979).
Niwas et al., Chemical Abstract No. 100:120922, Synthesis, 12, pp. 1027-8 (1983).
Oppolzer et al., Chemical Abstract No. 99:122722, Helv. Chim. Acta, 66(4):1119-28 (1983).
Pages et al., Chemical Abstract No. 87:23709, Bull. Soc. Chim, Fr., (11-12, Pt 2), pp. 1847-8 (1976).
Parker et al., Chemical Abstract No. 128:238972, J. Med. Chem., 41(6):1001-1005 (1998).
Parker et al., "Synthesis and Pharmacological Evaluation of Ring-Methylated Derivatives of 3,4-(Methylenedioxy) Amphetamine (MDA)," J. Med. Chem., 41:1001-5 (1998).
Rozwadowska Chemical Abstract No. 89:110062, Pol. J. Chem., 52(4):823-9 (1978).
Schales, Otto et al., "Arylnitroalkenes: A New Group of Antibacterial Agents," Journal of the American Chemistry Society, 74:4486-4490 (1952).
Schales and Graefe, "Arylnitroalkenes: A New Group of Antibacterial Agents," Chem. Res. Lab., Mar. 13, 1952.
Schlosser et al., Chemical Abstract No. 129:216547, Tertrahedron, 54(3):9023-32 (1998).
Schoeps et al., Chemical Abstract No. 119:265505, Nucl. Med. Biol., 20(5):669-78 (1993).
SciFinder Scholar results of patentability search conducted by Applicant, Feb. 15, 2002.
Sepulveda et al., Chemical Abstract No. 77:13885, J. Med. Chem., 15(4):413-15 (1972).
Shulgin Chemical Abstract No. 68:39275, Can. J. Chem., 46(1):75-7 (1968).
Shulgin, "Convenient Synthesis of Myristicinaldehyde," Can. J. Chem., 46:75-77 (1968).
Sy, Wing Wah et al., "Nitration of substituted styrenes with nitryl iodine." Tetrahedron Letters, Elsevier Amsterdam, NL, 26(9):1193-1196 (1985).
Van Eijk et al., Chemical Abstract no. 109:230661, Recl. Trav. Chim. Pays-Bas, 107(2):27-39 (1988).
Winn et al., Chemical Abstract No. 124:193286, J. Med. Chem., 39(5):1039-48 (1996).
Wolf et al., Chemical Abstract No. 114:101522, J. Med. Chem., 34(2):861-3 (1991).
Yang et al., Chemical Abstract No. 122:240114, Bioorg. Med. Chem. Let., 5(5):465-8 (1995).
Yoneda et al., Chemical Abstract No. 135:220642, Bioorganic & Medicinal Chem., 9(5):1197-1212 (2001).
Zee-Cheng et al., Chemical Abstract No. 70:37400, J. Med. Chem., 12(1):157-61 (1969).
Zhao et al., Chemical Abstract No. 116:99167, Chem. Reson. Toxicol., 5(1):89-94 (1992).

* cited by examiner

ANTIMICROBIAL AND RADIOPROTECTIVE COMPOUNDS

The present application is a continuation of U.S. patent application Ser. No. 12/776,896, filed May 10, 2010 (to issue), which was a continuation of U.S. patent application Ser. No. 11/923,404 filed Oct. 24, 2007 (now U.S. Pat. No. 7,825,145), which was a continuation of U.S. patent application Ser. No. 10/481,667 filed Aug. 26, 2004 (now abandoned), which was the national stage entry of PCT Intl. Patent Appl. No. PCT/AU02/00783, filed Jun. 14, 2002, which claimed priority to Russian Provisional Patent Appl. No. 2001/117033, filed Jun. 18, 2001. The content of each aforementioned priority application is specifically incorporated herein by reference in its entirety by express reference thereto.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

Bacterial, fungal and protozoal pathogens are responsible for a very wide variety of infections, ranging from minor respiratory ailments to fulminant systemic infections and chronic illnesses. Food poisoning caused by organisms such as *Salmonella* or *Campylobacter* is common, and is often associated with endemic infection in livestock or poultry raised using intensive animal husbandry techniques.

Despite the wide availability of antibiotics, control of infection is difficult, and many organisms have the ability to develop resistance. Many microorganisms cause problems which have hitherto proved to be quite intractable, such as multi-drug resistant *Staphylococcus aureus* infection in hospitals, drug-resistant *Enterococcus* infections, bacterial, fungal and protozoal infection in HIV patients, tuberculosis, and malaria and other endemic infections in underdeveloped countries.

Currently there are only very few agents which have a wide spectrum of activity against pathogens of bacterial, fungal and protozoal origin. Antibiotics are the most widely used agents in the fight against pathogenic microorganisms. However, most antibiotics have narrow specificity. Even broad spectrum antibacterial antibiotics are not very effective against fungi and protozoa. Most antibiotics belong to a restricted range of classes of compounds; although improved semi-synthetic derivatives of these have developed, only a few new antibiotic compound classes have become available in the last twenty years.

The choice of agents for protection of living organisms against radioactive radiation is also quite limited. Among the radiation protectors the most effective are sulphur-containing compounds (Kuna, 1989). For example, cystamine is approved for use as a radiation-protective agent (Vladimirov et al, 1989). The index of protection of this preparation does not exceed 1.45, and has the disadvantage that it causes diarrhoea. Another known radiation-protective preparation is mercamine (β-mercaptoethylamine) (Mashkovskiy, 1986). This has a low therapeutic index, short period of action (0.5-1 h), and short duration of radiation protecting activity (15-30 min).

It is known that β-nitrostyrene and some of its derivatives demonstrate biological, and partly fungicidal activity (Foyer, 1973). Russian Patent No. 2145215 showed that certain derivatives of arylnitroalkenes have antimicrobial, antifungal, antiprotozoal activity, and are able to provide protection from radiation damage. These compounds have the following formula

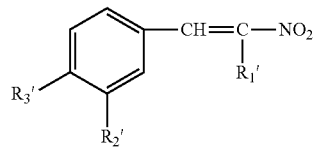

in which $R_1'$ is H or $CH_3$; and
$R_2'$ and $R_3'$ are the same or different and are selected from H, $OCH_3$, OH, $NO_2$ and $(CH_3)_2N$.

The activities of these compounds are satisfactory, but there is a need for low cost, low-toxicity agents with a wide spectrum of antimicrobial activities.

We have now found that certain substituted nitrostyrene compounds have excellent activity against very wide spectrum of organisms, including bacteria, fungi and protozoa and also have the ability to provide protection from radiation damage.

SUMMARY OF THE INVENTION

The invention provides a method of treatment and/or prophylaxis of a microbial infection, comprising the step of administering an effective amount of a compound of formula I:

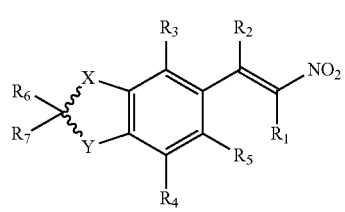

in which
X and Y are either the same or different and selected from a heteroatom;

⦃ is a double or single bond depending on the heteroatoms X and Y;

$R_1$ to $R_5$ are either the same or different and selected from hydrogen or a non-deleterious substituent; and $R_6$ and $R_7$ are either the same or different and selected from hydrogen and a non-deleterious substituent or one of $R_6$ and $R_7$ are absent when there is a double bond present, pharmaceutically acceptable salts or derivatives, prodrugs, tautomers and/or isomers thereof.

The invention also provides use of the compound of formula I in the manufacture of a medicament for the treatment and/or prophylaxis of a microbial infection.

The invention further provides use of the compound of formula I for the treatment and/or prophylaxis of a microbial infection.

The invention still further provides a method for protecting a subject from radiation damage which comprises administering an effective amount of the compound of formula I to a subject in need thereof.

In another aspect, the invention provides a method of cancer radiotherapy which comprises administering to a subject in need of such therapy an effective amount of the compound of formula I and subjecting the locus of a tumour in the subject to a radiation source.

In a further aspect, the invention provides use of the compound of formula I as an antimicrobial or radioprotective agent.

Preferably X and Y are either the same or different and selected from O and N, more preferably both X and Y are oxygen.

Preferably $R_1$ and $R_2$ are either the same or different and selected from hydrogen, hydroxy, halogen or optionally substituted $C_{1-6}$ alkyl.

$R_3$ to $R_5$ are preferably either the same or different and selected from hydrogen, hydroxy, halogen, nitro, $C_{1-6}$ alkoxy or optionally substituted $C_{1-6}$ alkyl.

Preferably halogen is chlorine or bromine.

The E isomer of the compounds of formula I is preferred.

Particularly preferred are compounds of the formula I in which X, Y, ⁑, $R_6$ and $R_7$ are as defined above; $R_1$ and $R_2$ are either the same or different and selected from hydrogen, hydroxy, Cl, Br and $C_{1-4}$ alkyl; and $R_3$ to $R_5$ are either the same or different and selected from hydrogen, hydroxy, Cl, Br, nitro, $C_{1-4}$ alkoxy or $C_{1-4}$ alkyl.

Specific examples of the compounds of the present invention are as follows:

(1) X and Y are O, $R_1$ is methyl and $R_2$ and $R_3$ are hydrogen (3,4-methylenedioxy-β-methyl-β-nitrostyrene)

1

(2) X and Y are O and $R_1$ to $R_3$ are hydrogen (3,4-methylenedioxy-β-nitrostyrene)

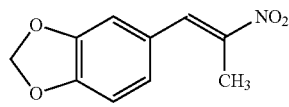

2

(3) X is N, Y is NH, $R_1$ is methyl and $R_2$ and $R_3$ are hydrogen (benzimidazole-5-β-nitropropylene)

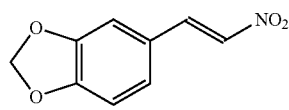

3

(4) X is N, Y is NH, $R_1$ is hydrogen, $R_2$ is methyl and $R_3$ is absent (2-methyl benzimidazole-5-β-nitroethylene)

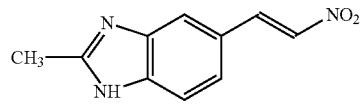

4

(5) X is O, Y is N, $R_1$ and $R_2$ are hydrogen and $R_3$ is absent (benzoxazole-5-β-nitroethylene)

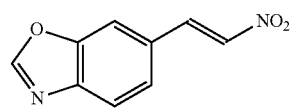

5

(6) X is N, Y is O, $R_1$ and $R_2$ are methyl and $R_3$ is absent (2-methyl benzoxazole-5-β-nitropropylene)

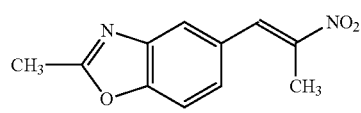

6

Some of the compounds of the formula I are novel per se. Accordingly, the invention provides a compound of formula Ia:

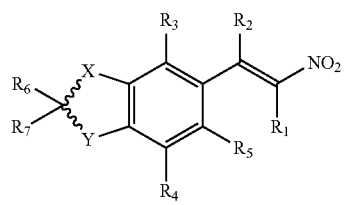

Ia in which X, Y, ⁑ and $R_1$ to $R_7$ are as defined in formula I above, with the provisos that when both X and Y are O and $R_2$ to $R_7$ are hydrogen, then $R_1$ is not hydrogen, $C_{1-4}$ alkyl or $CO_2Et$ or when both X and Y are O, then $R_1$ to $R_7$ are not hydrogen.

The invention also provides a process for the preparation of the compound of formula Ia defined above which comprises condensing a compound of formula II:

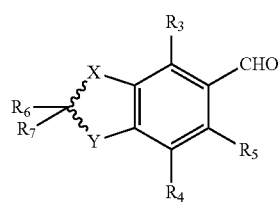

II in which X, Y, ⁑, $R_3$ to $R_7$ are as defined in formula Ia above with a compound of formula III:

$$R_1R_2CHNO_2 \qquad \text{III}$$

in which $R_1$ and $R_2$ are as defined in formula Ia above.

The invention further provides a process for the preparation of the compound of formula Ia defined above which comprises reacting a compound of formula IV:

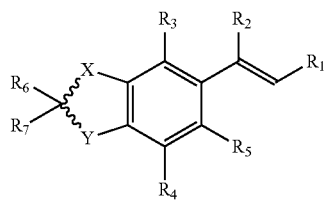

in which X, Y, ⧘, $R_1$ to $R_7$ are as defined in formula Ia above with $C(NO_3)_4$.

The processes are preferably performed in the presence of a catalyst, such as, an amine or an alkali metal hydroxide, for example, NaOH or KOH.

In a further aspect, the invention provides a pharmaceutical or veterinary composition comprising the compound of formula Ia defined above together with a pharmaceutically or veterinarily acceptable carrier.

Preferably, the pharmaceutical or veterinary composition is a topical, oral or parenteral composition.

The pharmaceutically or veterinarily acceptable carrier is preferably an organic solvent such as acetone, benzene, acetonitrile, DMSO or an alcohol, for example, methanol or ethanol. While the compounds of the present invention show a poor solubility in water, when water is combined with an organic solvent a stable mixture is formed.

DETAILED DESCRIPTION OF THE INVENTION

For the purposes of this specification it will be clearly understood that the word "comprising" means "including but not limited to", and that the word "comprises" has a corresponding meaning.

The term "heteroatom" denotes O, N or S.

The term "non-deleterious substituent" is used herein in its broadest sense and refers to a substituent which does not have a deleterious effect on the antimicrobial or radioprotective properties of the compound. Examples include alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, arylthio, acylthio and phosphorus-containing compounds.

Particularly suitable non-deleterious substituents are alkyl, alkenyl, alkynyl, halo, haloalkyl, haloalkenyl, haloalkynyl, hydroxy, alkoxy, alkenyloxy, haloalkoxy, haloalkenyloxy, nitro, nitroalkyl, nitroalkenyl and nitroalkynyl.

In a preferred embodiment the non-deleterious substituents are $C_{1-6}$ alkyl, halo, hydroxy, $C_{1-6}$ alkoxy and nitro.

The term "optionally substituted" means that a group may or may not be further substituted with, for example, the groups specified above under the definition of non-deleterious substituent.

The term "halogen" refers to fluorine, chlorine, bromine and iodine, preferably chlorine and bromine.

The term "alkoxy" is used herein in its broadest sense and refers to straight chain, branched chain or cyclic oxy-containing radicals each having alkyl portions, preferably $C_{1-6}$ alkyl, more preferably $C_{1-4}$ alkyl. Examples of such alkoxy groups are methoxy, ethoxy, propoxy, butoxy and t-butoxy.

The terms "$C_{1-4}$ alkyl" or "$C_{1-6}$ alkyl" used either alone or in compound words such as "optionally substituted $C_{1-4}$ or $C_{1-6}$ alkyl" refer to straight chain, branched chain or cyclic hydrocarbon groups having from 1 to 6 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl.

The salts of the compound of formula I or Ia are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the invention.

By "pharmaceutically acceptable derivative" is meant any pharmaceutically acceptable salt, hydrate or any other compound which, upon administration to the subject, is capable of providing (directly or indirectly) a compound of formula I or Ia or an antimicrobial or radioprotective active metabolite or residue thereof.

The term "pro-drug" is used herein in its broadest sense to include those compounds which are converted in vivo to compounds of formula I or Ia.

The term "tautomer" is used herein in its broadest sense to include compounds of formula I or Ia which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of formula I or Ia may have one or more chiral centres, it is capable of existing in enantiomeric forms.

The term "microbial infection" is used herein in its broadest sense and refers to any infection caused by a microorganism and includes bacterial infections, fungal infections, yeast infections and protozoal infections.

The term "microorganism" includes any microscopic organism or taxonomically related macroscopic organism within the categories algae, bacteria, fungi, yeast and protozoa or the like.

Bacterial infections include, but are not limited to, infections caused by *Bacillus cereus, Bacillus anthracis, Clostridium botulinum, Clostridium difficile, Clostridium*

*tetani, Clostridium perfringens, Corynebacteria diphtheriae, Enterococcus (Streptococcus* D), *Listeria monocytogenes,* Pneumoccoccal infections (*Streptococcus pneumoniae*), Staphylococcal infections and Streptococcal infections; Gram Negative bacteria including *Bacteroides, Bordetella pertussis, Brucella, Campylobacter* infections, enterohaemorrhagic *Escherichia coli* (EHEC/*E. coli* 0157: H7) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulare, Myobacterium johnei, Mycobacterium leprae,* atypical bacteria, *Chlamydia, Mycoplasma, Rickettsia, Spirochetes, Treponema pallidum, Borrelia recurrentis, Borrelia burgdorfii* and *Leptospira* icterohemorrhagiae and other miscellaneous bacteria, including *Actinomyces* and *Nocardia.*

Fungal infections include, but are not limited to, infections caused by *Alternaria alternata, Aspergillus flavus, Aspergillus fumigatus, Aspergillus nidulans, Aspergillus niger, Aspergillus versicolor, Blastomyces dermatiditis, Candida albicans, Candida dubliensis, Candida krusei, Candida parapsilosis, Candida tropicalis, Candida glabrata, Coccidioides immitis, Cryptococcus neoformans, Epidermophyton floccosum, Histoplasma capsulatum, Malassezia furfur, Microsporum canis, Mucor* spp., *Paracoccidioides brasiliensis, Penicillium marneffei, Pityrosporum ovale, Pneumocystis carinii, Sporothrix schenkii, Trichophyton rubrum, Trichophyton interdigitale, Trichosporon beigelii* and *Rhodotorula* spp.

Yeast infections include, but are not limited to, infections caused by *Brettanomyces clausenii, Brettanomyces custerii, Brettanomyces anomalous, Brettanomyces naardenensis, Candida himilis, Candida intermedia, Candida saki, Candida solani, Candida tropicalis, Candida versatilis, Candida bechii, Candida famata, Candida lipolytica, Candida stellata, Candida vini, Debaromyces hansenii, Dekkera intermedia, Dekkera bruxellensis, Geotrichium sandidum, Hansenula fabiani, Hanseniaspora uvarum, Hansenula anomala, Hanseniaspora guillermondii Hanseniaspora vinae, Kluyveromyces lactis, Kloekera apiculata, Kluveromyces marxianus, Kluyveromyces fragilis, Metschikowia pulcherrima, Pichia guilliermodii, Pichia orientalis, Pichia fermentans, Pichia memranefaciens, Rhodotorula Saccharomyces bayanus, Saccharomyces cerevisiae, Saccharomyces dairiensis Saccharomyces exigus, Saccharomyces uinsporus, Saccharomyces uvarum, Saccharomyces oleaginosus, Saccharomyces boulardii, Saccharomycodies ludwigii, Schizosaccharomyces pombe, Torulaspora delbruekii, Torulopsis stellata, Zygoaccharomyces bailli* and *Zygosaccharomyces rouxii.*

Protozoal infections include, but are not limited to, infections caused by *Leishmania, Toxoplasma, Plasmodia, Theileria, Anaplasma, Giardia, Trichomonas, Trypanosoma, Coccidia,* and *Babesia.* Specific examples include *Trypanosoma cruzi, Eimeria tenella, Plasmodium falciparum, Plasmodium vivax* or *Plasmodium ovale.*

Preferably, the microbial infection is an infection caused by either a Gram Positive or a Gram negative bacterium, for example, *Staphylococcus aureus, Enterococcus fecalis, Klebsiella pneumonia, Salmonella typhimurium* or *pseudotuberculosis, Acinetobacter, Pseudomonas aeruginosa, Clostridium perfringens, Clostridium difficile, Campylobacter jejuni* or *Bacteroides fragilis*; a fungal or yeast infection, for example, *Trichophyton interdigitale; Aspergillus fumigatus* or *Candida albicans*; or a protozoal infection, for example *Plasmodium falciparum* or *Trichomonas vaginalis.*

Examples of microbial infections include bacterial or fungal wound infections, mucosal infections, enteric infections, septic conditions, pneumonia, trachoma, ornithosis, trichomoniasis, fungal infections and salmonellosis, especially in veterinary practice. The compounds of the invention may also be used for the treatment of resistant microbial species or in various fields where antiseptic treatment or disinfection of materials is required, for example, surface disinfection.

The term "subject" as used herein refers to any animal having a disease or condition which requires treatment with a pharmaceutically-active agent. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the orders Primates, Rodentia, Lagomorpha, Cetacea, Carnivora, Perissodactyla and Artiodactyla. Members of the orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The order Perissodactyla comprises horses and donkeys, which are both economically important and closely related. Indeed, it is well known that horses and donkeys interbreed.

As used herein, the term "effective amount" is meant an amount of a compound of the present invention effective to yield a desired antimicrobial or radioprotective activity.

The specific "effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The term "radiation damage" is used herein in its broadest sense and refers to damage resulting from exposure to a radiation source, such as, ionising radiation. The term "ionising radiation" as used herein refers to photons having enough energy to ionise a bond, such as, $\alpha$, $\beta$ and $\gamma$ rays from radioactive nuclei and x-rays.

The term "cancer radiotherapy" is used herein in its broadest sense and include radiotherapy involving tumours which may be either benign or malignant.

The primary application of the radioprotector of the present invention is in cancer radiotherapy. Many of the normal tissues which are a problem in radiotherapy such as the skin, oral mucosa, oesophageal mucosa, rectal mucosa, vaginal mucosa and bladder epithelium can be protected by the radioprotectors of the present invention.

Outside the context of cancer radiotherapy, the radioprotectors of the present invention could be used prophylactly in high risk radiation situations.

The compounds of the present invention may additionally be combined with other medicaments to provide an operative combination. It is intended to include any chemically compatible combination of pharmaceutically-active agents, as long as the combination does not eliminate the activity of the compound of formula I or Ia. It will be appreciated that the compound of the invention and the other medicament may be administered separately, sequentially or simultaneously.

Other medicaments which may be used when treating microbial infections include other anti-infective agents such as antibiotics.

When the compounds are used as radioprotectors the other medicaments may include chemotherapeutic agents, for example, radiomimetic agents which are cytotoxic agents that damage DNA in such a way that the lesions produced in DNA are similar to those resulting from ionising radiation. Examples of radiomimetic agents which cause DNA strand breaks include bleomycin, doxorubicin, adriamycin, 5FU, neocarcinostatin, alkylating agents and other agents that produce DNA adducts. It is anticipated that the radioprotectors of the present invention will protect DNA from damage by some of these agents, in the same way as they protect against the effects of ionising radiation. In clinical applications, it is unlikely that the radioprotector would be administered systemically together with the chemotherapeutic agent, since this could compromise the action of this agent on the tumour. However, there are circumstances where topical application to problem tissues could be advantageous. For example, oral mucositis is problem side-effect for cytotoxic agents, such as, doxorubicin and administration of the present radioprotector as a mouth-wash before administration of the chemotherapeutic agent could ameliorate this side-effect without compromising the action of this agent on a tumour not located in the oral cavity. Similarly, the gastrointestinal tract could be protected by oral administration, the lungs by aerosol inhalation or the bladder by intravesical delivery, for example, via a catheter of the radioprotector. Hence a preferred method in accordance with the present invention utilises the compound of formula I or Ia in conjunction with another medicament, such as, a radiomimetic agent.

The compounds of the invention may be conjugated to agents, for example, via the interactive group, which will specifically deliver them to a desired tumour site. Suitable agents may include antibodies or proteins, growth factors, for example, haemopoietic growth factor which will enable preferential radioprotection of haemopoietic stem cells to occur in the context of total body irradiation and bone marrow transplantation.

There is also an ex vivo application of the conjugates of the compounds of the invention in the context of bone marrow transplantation. Bone marrow transplantation generally involves obtaining and storing bone marrow samples from a subject in anticipation of a deterioration of their condition. A rather drastic form of chemotherapy (i.e. a high dose) is then administered. This chemotherapy is such that it would normally be lethal due to the destruction of normal stem cells, but the subject is rescued by the administration of their own haemopoietic stem cells. The problem with this procedure is that the initial sample of stem cells is likely to be contaminated with tumour cells and various procedures are use therefore to purge the bone marrow preparations of the tumour cells. Radioprotectors conjugated to a haemopoietic growth factor could be used in this context by being added to a suspension of bone marrow cells. The suspension could then be irradiated in the expectation that the normal bone marrow cells, but not the tumour cells, would be preferentially protected from the cell-killing effects of the radiation.

As used herein, a "pharmaceutical carrier" is a pharmaceutically acceptable solvent, suspending agent or vehicle for delivering the compound of formula I or Ia to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I or Ia may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques.

The present invention also provides suitable topical, oral and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I or Ia as well as the pharmaceutically-active agent useful in the method of the invention can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump. For in vitro studies the agents may be added or dissolved in an appropriate biologically acceptable solvent or buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The invention includes various pharmaceutical compositions useful for ameliorating disease. The pharmaceutical compositions according to one embodiment of the invention are prepared by bringing a compound of formula I or Ia, analogues, derivatives or salts thereof, or combinations of compound of formula I or Ia and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Williams (2000), the British National Formulary, $43^{rd}$ edition (British Medical Association and Royal Pharmaceutical Society of Great Britain, 2000), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the microbial infections. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compound of formula I or Ia may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compound of formula I or Ia may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Dosage levels of the compound of formula I or Ia of the present invention may be of the order of up to about 1 g per kilogram body weight. The amount of active ingredient that may be combined with the carrier materials to produce a single dosage will vary depending upon the host treated and the particular mode of administration. For example, a formulation intended for oral administration to humans may contain up to about 1 g of an active compound with an appropriate and convenient amount of carrier material which may vary from about 5 to about 95 percent of the total composition. Dosage unit forms will generally contain between from about 5 mg to about 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10-50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

Figure 1:
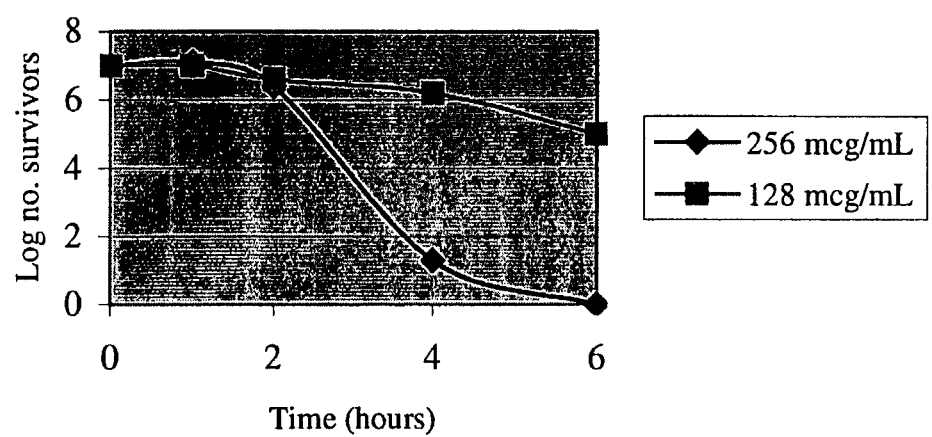
FIG. 1 is a graph of Log. No. survivors vs time (hours) for *Candida albicans* in Example 9.

The invention will now be described in detail by way of reference only to the following non-limiting examples and drawings.

Example 1

General Synthesis Methods

Benzdioxols are described in the literature (Perekalkin, 1982a). The synthesis of benzoimidazole and benzoxazole may also be carried out using standard condensation methods 1 and 2 (Perekalkin, 1966, 1982b) as shown below.

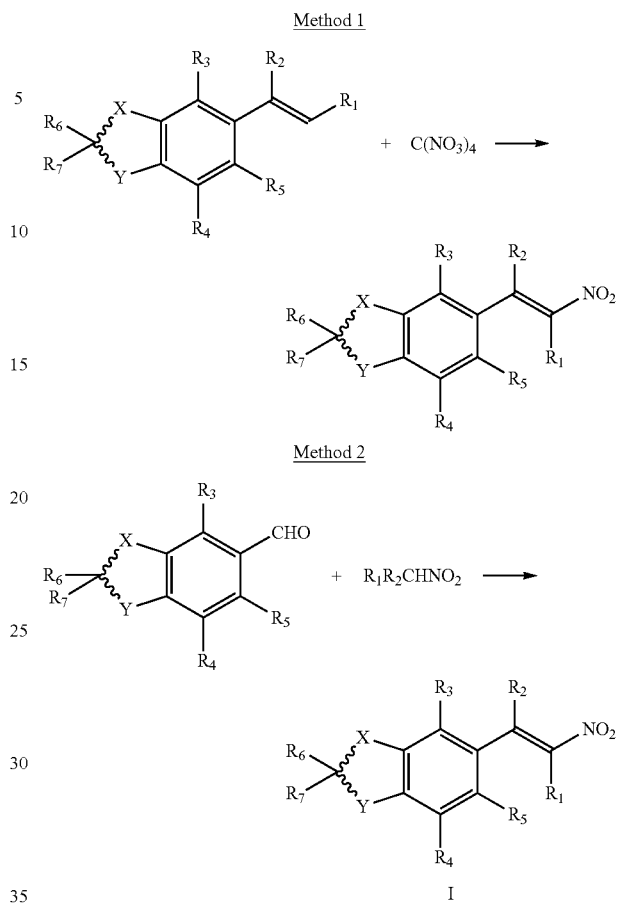

in which X, Y, ⌇ and $R_1$ to $R_7$ are as defined in formula I above.

In Method 2, equimolecular quantities of benzaldehyde and nitroalkane were mixed in an Erlenmayer flask and dissolved in equal volume of alcohol. Fresh distillated ethylenediamine was added to the obtained solution in catalytical quantities (usually 1:10 in relation to aldehyde and nitroalkane) and was left in the dark at room temperature for several days (from 3 up to 10 days). During this time compound crystallised. After the cooling up to about 0° C., the crystals were filtrated and washed with cold alcohol and then dried. When the yield is small, the mother liquids can be joined together and evaporated in rotary evaporator. After cooling the additional quantity of impure product is obtained. The product was purified by dissolving in a minimal quantity of boiling alcohol. It was then treated with activated carbon, filtered hot and while the cooling was in progress, fine yellow needles crystallised. The yield was about 80-85%, the compound being chromatographically homogeneous.

The infrared spectra of the compounds obtained are in accordance with those described in the literature (Hamlin and Weston, 1949; Knoevenagel and Walter, 1904; Burton and Duffield, 1949).

The compounds were soluble in organic solvents such as ethanol, acetone, benzene, methanol, acetonitrile, chloroform and DMSO, but showed very poor solubility in water (0.1%). When an alcoholic solution was added to water, a stable colloidal mixture was formed.

Example 2

Method for Preparing Compound (1) (3,4-methylenedioxy-β-methyl-β-nitrostyrene)

Compound (1) was prepared using Method 1 described in Example 1 above. The reaction scheme is shown below.

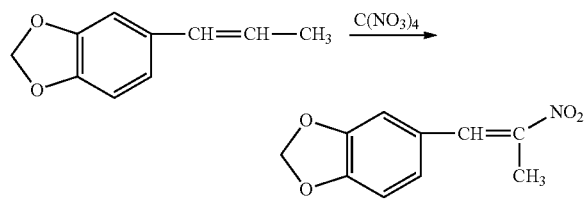

A mixture of 9.8 g of tetranitromethane (1 mole) and 10 cm³ of acetone was cooled by ice and added dropwise to 8.1 g of distilled isosafrole (1 mole) and 4.8 g of pyridine (1.2 mole) dissolved in 20 cm³ of acetone. The very first drops caused darkening of the reaction mixture and the liquid turned non-transparent and murky red when the entire portion of tetranitromethane was added. The smell of tetranitromethane disappeared quickly and in approximately 2 hours the dark red solution which had turned transparent was poured into 100 cm³ of water in a stoppered bottle. The mixture was thoroughly shaken, covered with a layer of ether and a mixture of 6.7 cm³ of 33% solution of caustic potassium (1.03 mole) and 50 cm³ of water was added in small portions. The mixture was shaken after each addition and once the entire amount of alkali was added, the shaking was continued until the entire salt of pyridine and nitroform, which is present as a dark red oil, disappeared. The water layer was then separated and again extracted with ether. Combined ether extracts were first rinsed with water and then with water acidified with sulphuric acid and finally once again with pure water. After distillation of the ether in the vacuum, a sediment of β-nitroisosafrole was to be found in the form of yellow needles, which were re-crystallized from approximately 65 cm³ of alcohol. Compound (1) was obtained with a melting point of 98° C. and a yield of 7 g. Once the solvent had evaporated, another 0.5 g of Compound (1) was obtained. The total product amounted to 72.5% of the theoretical yield.

Example 3

Alternative Method for Preparing Compound (1) (3,4-methylenedioxy-β-methyl-β-nitrostyrene)

Compound (1) was prepared using Method 2 described in Example 1 above. The reaction scheme is shown below.

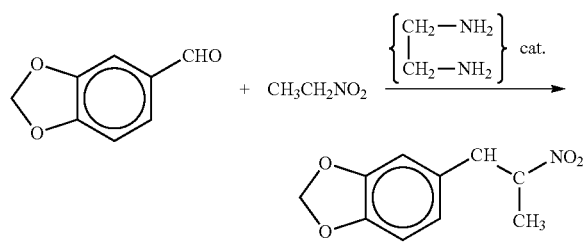

900 gm piperonal was dissolved in 1000 cc alcohol with constant shaking and 450 ml nitroethane was added slowly followed by 10 ml ethyldiamine. After 17 hrs stirring, the mixture was placed in the dark at room temperature for 5-7 days. The resulting yellow crystals were filtrated in a Buchner funnel until dried and then washed twice with 150 ml alcohol. This yielded 1200 gm of Compound (1) with melting point of 95° C. After further crystallization from ethanol, 1000 gm of light yellow crystals were obtained with a melting point of 98° C. (approx 80% yield).

Molecular formula $C_{10}H_9NO_4$, molecular weight—207.05
Physical and Chemical Characteristics
Form of state yellow crystals
Solubility profile <soluble in ethanol, acetone, benzene, methanol, acetonitrile, chloroform, DMSO
—almost insoluble in water
Melting point 94-98° C. (when crystallized from 50% ethanol product had 96-98° C.)
pH (in 50% v/v ethanol) approximately neutral
Specific rotation optically inactive but has 2 stereoisomers
Stability begins to darken above 200° C.
Purity MS indicates impurities of molecular weight 303.4 & 331.4 to be the major impurities
IR Spectrum
1. Aromatic ring—above 3000 wave number & associate aromatics 1470-1630 region
2. β-methylstyrene—additional groups over styrene 1442 aliphatic —C—+900-1000 peaks
3. Nitrogroup at low wave number e.g. 747, 673 and β-nitrostyrene has 1520.
4. Aromatic Ether Group—1312 (1258) 1138, 1030 Nevertheless a fingerprint of this compound is provided by the IR spectrum (q.v.). This has been done on the recrystallised material in order to reduce peaks due to contaminants.
IR Spectrum
Impurities of molecules weight 303.4 & 331.4 Confirmation of molecular weight of main species 207.1
NMR Spectrum
Hydrogen NMR (200 MHz) shows:
Aromatic ring with 3 remaining Hs, 3 Hs as part of a $CH_3$, another attached to the side chain and 2 Hs as part of another ring.
Carbon NMR (50 MHz) shows:
—$CH_3$, CH—, —$CH_2$ (as methylenedioxy)
Values of chemical shifts support the structure given and a likelihood of the E-stereoisomer rather than the Z-stereoisomer favoured by the synthesis used. A strong-withdrawing group ($NO_2$) is indicated.
UV/Visible Spectrum
Recrystallised material has peaks (broad) at 250-270 mm and 360-370 mm with high absorbance below 210 mm.

Example 4

Process for Preparing Compound (2)

Compound (2) was prepared using Method 2 described in Example 1 above. The reaction scheme is shown below.

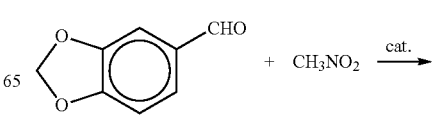

-continued

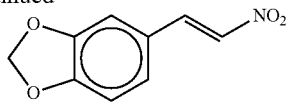

3,4-methylenedioxybenzaldehyde was condensed with nitromethane using fresh distillated ethylenediamine NH$_2$—CH$_2$—CH$_2$—NH$_2$ as a catalyst. The reaction was conducted in alcohol, darkness and at room temperature for 5 days. The resultant crystals were separated by filtration and washed with cold alcohol. After being dried in air, the yield was 80%, m.p.—158-159° C. and after re-crystallization the m.p. was 162-163° C. Compound (2) was non-soluble in water, soluble in acetone, alcohol, acetic acid and in a majority of organic solvents.

Example 5

Antibacterial Activity

In the experiments described herein, museum strains of pathogens obtained from the museum of the Microbiology chair of the Military Medical Academy (designated by the index "M") and strains selected from pathological material (designated by the index "B"), taken from patients and having gone through no more than three laboratory passages were used. For each type of pathogen the corresponding optimal nutrient media was used. For the impregnation method, compounds (1) and (2) were added to solid nutrient media at doses from 0.03% to 2.0%. An agar diffusion assay analogous to the standard method of determining sensitivity to antibiotics was used.

The agar diffusion assay was performed as follows.

Meat peptone agar was prepared and impregnated with the test compounds at concentrations from 0.01 to 2.0%. The medium was poured into Petri dishes and allowed to set. Agar plugs of 10 mm diameter were cut out and placed on the surface of Petri dishes containing the same medium immediately after they were inoculated with the microorganisms to be investigated (at least 6 plugs per culture). After one day of incubation at 37° C., the diameter of the zone of retardation of growth of the culture around the plugs was measured. The results were evaluated in accordance with official standards of testing sensitivity to antibiotics; a diameter≤20 mm corresponded to a stable culture, 21-28 mm to moderate stability and ≥29 mm to sensitivity.

In parallel to this, the sensitivity of pathogens to 15 antibiotics were tested according to the official protocol of the Russian Supervisory Authority for the Introduction of New Medicinal Substances and Medical Technology (disc method).

Several pathogen types and strains were used to show the limits of sensitivity of the strains and types to the test substances, in order to evaluate their probable overall breadth of performance.

Table 1 below shows the results of experiments with Compound (1) at a concentration of 1.0%, at which it suppressed the propagation of 5×10$^5$-5×10$^7$ organisms/mL, and comparative results of sensitivity experiments using the following 15 antibiotics:

1—penicillin,
2—ampicillin,
3—gentamycin,
4—carbenicillin,
5—kanamycin,
6—lincomycin,
7—levomicethin,
8—oxacillin,
9—polymixin,
10—rifampicin,
11—ristomycin,
12—streptomycin,
13—tetracycline,
14—erythromycin,
15—cephalosporin.

TABLE 1

| | Compound | Suppression of Growth (+/−) Antibiotics | | | | | | | | | | | | | | |
|---|---|---|---|---|---|---|---|---|---|---|---|---|---|---|---|---|
| Microorganism | (1) | 1 | 2 | 3 | 4 | 5 | 6 | 7 | 8 | 9 | 10 | 11 | 12 | 13 | 14 | 15 |
| 1. Conditional pathogenic enterobacteria gram-negative aerobic bacilli | | | | | | | | | | | | | | | | |
| Pseudomonas aeruginosa B-601 | + | − | − | − | − | − | − | − | ± | − | − | ± | − | ± | − | − |
| Escherichia coli M-17 | + | + | + | + | + | + | − | + | − | + | − | − | ± | + | + | + |
| Escherichia coli B-683 | + | + | + | + | + | + | − | + | − | + | − | − | ± | + | + | + |
| Escherichia coli B-65 | + | + | + | + | + | + | + | + | − | + | − | + | ± | + | + | + |
| Enterobacter aerogenes B-679 | + | − | − | − | − | − | − | − | − | + | − | − | − | − | − | − |
| Enterobacter aerogenes B-687 | + | − | − | − | − | − | − | − | − | + | − | − | − | − | − | − |
| Citrobacter diversus B-678 | + | − | + | + | − | + | − | + | − | ± | − | − | ± | ± | − | + |
| 2. Pathogenic gram-negative bacteria | | | | | | | | | | | | | | | | |
| Shigella flexneri M-2A6907 | + | − | ± | + | ± | ± | − | + | − | ± | ± | − | ± | ± | − | ± |
| Shigella sonnei B-720 | + | − | ± | − | ± | ± | − | ± | − | ± | ± | − | ± | ± | − | ± |
| Salmonella typhimurium M-727 | + | − | − | − | ± | ± | − | − | − | ± | ± | − | ± | ± | − | ± |

TABLE 1-continued

|  | Compound | Suppression of Growth (+/−) | | | | | | | | | | | | | | |
|---|---|---|---|---|---|---|---|---|---|---|---|---|---|---|---|---|
|  |  | Antibiotics | | | | | | | | | | | | | | |
| Microorganism | (1) | 1 | 2 | 3 | 4 | 5 | 6 | 7 | 8 | 9 | 10 | 11 | 12 | 13 | 14 | 15 |
| *Salmonella paratyphi* M-16469 | + | − | ± | − | ± | ± | − | ± | − | − | − | − | ± | ± | − | ± |
| *Acinetobacter* B-681 | + | − | − | − | − | − | − | − | − | − | + | − | − | − | − | − |
| *Acinetobacter* B-676 | + | − | − | − | − | − | − | − | − | − | + | − | − | − | − | − |
| *Acinetobacter* B-677 | + | − | − | − | − | − | − | − | − | − | + | ± | − | − | − | − |
| *Alkaligenes* sp. B-689 | + | − | − | + | − | + | − | + | − | − | − | − | ± | − | − | − |
| *Alkaligenes* sp. B-667 | + | − | − | − | − | − | − | − | − | + | + | − | − | − | − | − |
| 3. Gram-negative non-fermenting bacteria | | | | | | | | | | | | | | | | |
| *Yersinia pseudotuberculosis* | + | − | − | − | − | − | − | − | − | − | − | − | − | − | − | − |
| *Klebsiella pneumoniae* M-A21 | + | − | − | − | − | − | − | − | − | − | − | − | − | − | − | − |
| *Klebsiella pneumoniae* M-248 | + | − | − | − | − | − | − | − | − | − | − | − | − | − | − | − |
| 4. Gram-negative aerobic bacilli | | | | | | | | | | | | | | | | |
| *Corynebacterium diptheriae* B-670 | + | − | ± | + | − | − | − | ± | − | − | + | + | − | + | + | + |
| *Bacillus* sp. B-575 | + | − | − | ± | − | ± | + | + | − | − | ± | ± | ± | + | ± | − |
| 5. Gram-positive aerobic cocci (*Neisseria*) | | | | | | | | | | | | | | | | |
| *Neisseria meningitidis* M-6231 | + | − | − | − | − | − | − | − | − | − | − | − | − | − | − | − |
| *Neisseria meningitidis* M-A72 | + | − | − | − | − | − | − | − | − | − | − | − | − | − | − | − |
| 6. Gram-positive cocci (Staphylococci) | | | | | | | | | | | | | | | | |
| Staphylococci *aureus* M-12159 | + | + | − | + | + | + | − | − | + | − | + | + | + | − | − | + |
| Staphylococci *aureus* M-209 | + | + | − | + | + | + | − | − | − | + | + | + | + | − | − | + |
| Staphylococci *aureus* B-685 | + | − | − | + | + | + | − | − | + | − | + | + | + | − | − | + |
| Staphylococci *aureus* B-674 | + | − | − | + | − | − | − | + | − | − | − | − | ± | + | + | + |
| Staphylococci epidermidis D-513 | + | + | + | + | + | − | + | − | + | − | + | + | − | − | − | + |
| Staphylococci epidermidis BK-30 | + | + | + | − | + | − | − | − | + | − | + | + | − | − | − | − |
| 7. Gram-positive cocci (Streptococci) | | | | | | | | | | | | | | | | |
| γ-haemolytic *streptococcus* B-672 | + | + | + | − | − | − | − | − | − | − | − | + | − | − | − | − |
| β-haemolytic *streptococcus* B-624 | + | + | + | − | + | − | − | − | − | − | + | + | − | − | − | − |

Remarks:
+ sensitive strains
± moderately sensitive strains
− stable strains

Table 2 below shows the results of experiments on sensitivity of some microorganisms to Compound (1) using the agar diffusion method described above.

TABLE 2

Diameter of zone of Growth inhibition (mm)

| Microorganism | Concentration in disc of Compound (1) (%) | | |
|---|---|---|---|
| | 2.0 | 1.0 | 0.1 |
| γ-haemolytic streptococcus B-672 | 35# | 34# | 32# |
| β-haemolytic streptococcus B-624 | 31# | 32# | 31# |
| Staphylococci aureus B-685 | 39# | 37# | 35# |
| Staphylococci epidermidis B-513 | 38# | 34# | 32# |
| Shigella flexneri M-2A6907 | 36# | 33# | 31# |
| Shigella sonnei B-720 | 39# | 35# | 30# |
| Salmonella typhimurium M-727 | 32# | 30# | 24# |
| Salmonella paratyphi M-16469 | 36# | 30# | 28# |
| Acinetobacter B-681 | 38# | 35# | 32# |
| Alkaligenes sp. B-689 | 40# | 38# | 36# |
| Enterobacter agglomerans B-679 | 33# | 30# | 25# |
| Corynebacterium B-670 | 40# | 35# | 31# |
| Bacillus sp. B-575 | 38# | 34# | 29 |

Remarks:
sensitive
+ moderately sensitive
− stable

Table 3 shows the results of experiments of sensitivity of pathogenic fungi to compound (1).

TABLE 3

| Fungi | Dosage of Inoculation | Result | Number of microbes in the presence of Compound (1) at concentration (%) | | |
|---|---|---|---|---|---|
| | | | 2.0 | 0.5 | 0.1 |
| Candida albicans B-45 | 5 × 10$^4$ | Growth | 0 | 0 | 0 |
| | | Retardation | 5 × 10$^4$ | 5 × 10$^6$ | 5 × 10$^6$ |
| Candida albicans M-3 | 5 × 10$^4$ | Growth | 0 | 0 | 0 |
| | | Retardation | 5 × 10$^6$ | 5 × 10$^6$ | 5 × 10$^6$ |
| Trichophyton | 10$^2$ | Growth | 0 | 0 | 0 |
| | | Retardation | 10$^7$ | 10$^7$ | 10$^7$ |
| Geotrichum M-158 | 10$^5$ | Growth | 0 | 0 | 0 |
| | | Retardation | 10$^5$ | 10$^5$ | 10$^4$ |
| Torula histolytica (Cryptococcus) | 10$^5$ | Growth | 0 | 0 | 0 |
| | | Retardation | 10$^5$ | 10$^5$ | 10$^5$ |

Example 6

Antimicrobial Tests

The antimicrobial activity of Compound (1) was tested, using the agar diffusion method.

Due to the very low solubility of the compounds, the studies could not be carried out in the liquid phase. For this reason an initial mother impregnate, containing 0.5% of test compound, was prepared on meat peptone agar. From this mother impregnate, regenerated to the liquid state in a water bath, serial double dilutions were prepared by addition of the agar base. The dilutions thus obtained, containing the compounds in concentrations of 0.5%, 0.25%, 0.12%, 0.06%, 0.03%, 0.015% were poured into Petri dishes, on which 6 bacterial and 2 fungal test cultures were inoculated.

The following test cultures were used:
1) *Staphylococcus aureus* strain 674, isolated from a patient, sensitive to gentamycin, oxacillin, tetracycline, erythromycin and cephalothin, slightly sensitive to streptomycin.
2) *Enterococcus faecalis* museum strain, sensitive to ampicillin, rifampicin, and streptomycin.
3) *Klebsiella pneumoniae* strain 312, isolated from a patient, sensitive to gentamycin and polymyxin.
4) *Salmonella typhimurium* museum strain 727, sensitive to ampicillin, gentamycin, carbenicillin, canamicillin, polymyxin, and cephalothin.
5) *Acinetobacter* strain 681, isolated from a patient, slightly sensitive to polymyxin.
6) *Pseudonomas aeruginosa* strain 328, isolated from a patient, slightly sensitive to polymyxin.
7) *Trichophyton interdigitale*.
8) *Candida albicans*.

Each of the 8 test cultures was sown on sterile meat peptone agar in a Petri dish, and then a standard plug of agar, impregnated with one of the 9 compounds at a concentration of 0.5%, was placed on the agar surface. The retardation zone was measured around the plug after 24 h and 48 h growth at 37° C. For the fungal cultures the results were assessed after 7-10 days of incubation at 30° C.

The results of the action of the compound on the impregnated agar are summarised in Table 4.

TABLE 4

| | Minimal % Compound (1) giving complete inhibition of test culture | % inhibition by antibiotic |
|---|---|---|
| S. aureus | 0.015 | 5.5 |
| Enterococcus faecalis | 0.015 | 3 |
| Klebsiella pneumoniae | 0.12 | 2 |
| Salmonella typhimurium | 0.5 | 5 |
| Acinotobacter | 0.12 | 1 |
| Pseudomonas | — | 1.5 |
| Trichophyton | 0.25 | — |
| Candida | 0.5 | — |
| Activity Index | 0.4 | — |

Table 5 below shows the results of the agar diffusion experiments.

TABLE 5

Results of growth retardation by the compounds in the diffusions in the agar experiment

| Test culture | Size of zone of retardation of the growth by Compound (1) |
|---|---|
| Staphylococcus aureus | 6.5 |
| Enterococcus fecalis | 6 |
| Klebsiella pneumonia | 5 |
| Salmonella typhimurium | 7 |
| Acinetobacteria | 6.5 |
| Pseudonomas | 0 |
| Average zone of retardation | 5.17 |

In equal concentration Compound (1) inhibits the growth of ampicillin-resistant *Staphylococcus* and the growth of *Enterococcus* which is sensitive to this antibiotic. Similar differences can be observed with other pathogens and other preparations.

Anti TB Effects of Compound (1)

Anti TB effect was checked by standard method of serial double dilutive in synthetic liquid medium (SOTON) with 10% normal equine serum. The solution was prepared in Tween 80.

Test culture was Mycobact tub. H.37RV sensitive to anti TB medication.

Mycobacterial suspension (density $5 \times 10^7$ cells/ml) was spread onto a special liquid medium (Vischnevsky, B.I.)

Results were calculated for 10-14 days incubation at 37° C. MIC (totally inhibiting *M. tuberculosis*)

The results are shown in Table 6 below.

TABLE 6

|  | Minimal Inhibitory Concentration (μg/ml) |
| --- | --- |
| Compound (1) | 6.25 |
| Isoniazid | 0.02-0.1 |
| Rifampicin | 0.01-0.02 |
| Ethambutol | 1.0-2.5 |
| Streptomycin | 0.5 |

Only Compound (1) had MIC close to Ethambutol/Isoniazid MIC.

Example 7

Anti-Protozoal Activity

The effect of the Compounds (1) and (2) on trichomonas was also investigated. *Trichomonas vaginalis* isolated from patients was used. The trichomonads were cultured at pH 5.8-6.5 and 37° C. in medium 199 containing 5.0% native foetal calf serum, carbohydrates, and antibiotics to suppress the accompanying flora. Vaseline was applied to the surface of the medium in the culture tube. The experimental specimens contained the test compounds at a concentration of 0.3%.

7 specimens were investigated, containing motile forms of the parasite in a quantity of 5-8 cells in 1.0 cm$^3$. In the control, parasites were cultured successfully over 3-4 passages (each passage 5-6 days). In contrast, culture of motile forms in medium containing the test compounds was unsuccessful in every case. After only one passage in the presence of the test compounds, motile forms did not propagate.

Example 8

Anti-Bacterial Activity In Vivo

The therapeutic and prophylactic effect of the substances was determined in experiments in vivo on mice, infected intraperitoneally or intranasally with *Corynebacterium paratuberculosis*.

Compounds (1) and (2) were administered intraperitoneally, intramuscularly and orally at a dose of <20% LD$_{50}$/0.2 at different periods from the day of infection, ie 2 and 1 days before the infection (schedules 2, 1), on the day of infection (schedule 0) and 1, 2, 3 etc. days after the infection (schedules +1, +2, +3, etc).

The daily mortality rate was measured, their cumulative variations were calculated and based on this the results of the performance of the preparation was determined by the formula $AI=[(B-A):B] \times 100$ where AI=activity index of the preparation (%),
A=cumulative mortality in the experimental group,
B=cumulative mortality in the control group.

The results are shown in Table 7 below and indicate that Compounds (1) and (2) tested showed therapeutic and prophylactic activity in mice infected with *Corynebacterium paratuberculosis*.

For intramuscular administration, the clinical prophylactic performance in the form of reduced mortality of animals was 52.53%. The clinical performance for salmonellosis varied within the limits of 50.0-20.0%. For pseudotuberculosis the prophylactic performance was 50.0%.

TABLE 7

Order of activity of compounds as assessed by AI

| Compound | Pathogen and method of infection | Schedule of introduction of the preparation | Incubation period days (test/control) | | Cumulative mortality (test/control) | | Activity index % |
| --- | --- | --- | --- | --- | --- | --- | --- |
|  |  |  | test | contr. | test | contr. |  |
| 1 | *Salmonella* intraperitoneally | −1, 0, +1, +2, +3 200 mg/kg intramuscularly | 0 | 0 | 47 | 99 | +52.53 |
| 2 | *Salmonella* intranasally | +2, +3 200 mg/kg intramuscularly | 1 | 0 | 15 | 30 | +50.00 |

Example 9

Radiation Protective Activity

The radiation protective performance of the Compounds (1) and (2) investigated was tested on male white mice weighing 18-20 g.

Dosages: 2, 4, 6, 8, 10, 15, 20 Gr (1 hR=100 Röntgen).
Period of observation=25 days.
Method of reporting: dynamic mortality, calculation of cumulative mortality and factual changes of dosage (FCD).
Schedule of introduction: 50 mg/kg at 0.2 mL in mice.
Group 1—control,
Group 2—2 and 1 days up to irradiation.
Table 8 shows the results of the experiments on radiation performance of the compounds investigated.

TABLE 8

| | Cumulative mortality in groups % | |
| --- | --- | --- |
| Dosage R (hR*) | control | prophylactic |
| 2 | 2.9 | 0 |
| 4 | 3.6 | 0 |
| 6 | 13.1 | 3.8 |
| 8 | 21.1 | 9.5 |
| 10 | 43.8 | 13.3 |
| 15 | 66.7 | 45.5 |
| 20 | 94.1 | 83.3 |
| FCD |  | 1.39 + 1.48 |
| LD$_{50}$ | 10.73 hR | 15.88 hR |

Remarks:
*1 hR = 100 Rontgen

The results show that for all irradiation dosages prophylactic administration of the test compounds considerably decreases the mortality of irradiated animals in comparison with the control group. FCD (LD$_{50\ contr.}$)=1.39-1.43, which shows a high radiation protective effect of the compounds indicated, the performances of which do not yield to the reported media.

Example 10

Treatment of Infected Wounds

Human volunteers suffering from skin wounds infected by *Streptococcus* and *Staphylococcus* were treated with 0.1% Compounds (1) and (2) in an ointment base of vaseline, sheep fat and sulfoxide. Application of 0.1% ointment for 3 days cleared the wound completely of pus, with subsequent healing of the wound.

In 3 cases extensive damage to the skin caused by fungal infection was treated; the type of the fungus was not identified. The damaged area was smeared twice per day with 0.1% ointment. The skin was cleared of fungal growth within a week.

Example 11

Pharmacokinetics

While the pharmacokinetics of the compounds of the invention have not been investigated in detail, in experiments carried out in mice to which Compounds (1) and (2) were administered intraperitonally and intragastrically, it has been established that the compound will remain in a biologically active concentration in the blood for longer than 24 h.

Example 12

Toxicology

The average lethal dose for mice when administered intragastrically was 1500 mg/kg body weight; when administered intraperitonally the average lethal dose was 575 mg/kg body weight. Thus the compounds of the invention have low toxicity.

Example 13

Antimicrobial Activity and Solubility of Compound (1)

Compound (1) is relatively insoluble in water but is soluble in 10% DMSO at 1 mg/mL (0.1%), 10% ethanol at 2 mg/ml and 10% acetone at 2 mg/mL.

The highest concentration testable is either 512 µg/mL at 5% solvent or 256 µg/mL at 2.5% solvent. It does not require specific chemical neutralization, dilution being sufficient to neutralize residual activity in microbicidal testing.

DMSO was selected as the solvent for testing because it has the lowest toxicity against test strains.

Compound (1) was at least 8 times more active against *E. coli* when formulated in ethanol, giving an MIC of 128 µg/mL (0.06% ETON) compared to >512 µg/mL (2.5% DMSO). Ethanol is toxic to *E. coli* at concentrations >2.5%.

Example 14

Antibacterial Activity of Compound (1)

NCCLS-USA Standard Method—Broth microdilution (or macrodilution) (Mueller-Hinton).

Inoculum $1-4\times10^4$ cfu (or $-4\times10^5$ cfu). Ciprofloxacin test control. Chlorhexidine values added for disinfectant and antiseptic activity comparison.

Minimum inhibitory concentration (MIC) and minimum bactericidal concentration (MBC) as 3 log reduction (99.9% kill) at 35° C., 24 hours, aerobically (unless otherwise indicated). 48 h titres were not significantly different.

Results are shown in Table 9.

Summary of Results

Compound (1) is a relatively broad spectrum antibacterial agent with bactericidal activity within an acceptable concentration range in vitro for a representative selection of Gram positive and Gram negative bacteria. Compound (1) is broadly effective against aerobic Gram positive and Gram negative cocci and aerobic Gram positive rods of clinical significance.

Infections with Resistant Gram Positive Cocci

Clinical isolates (multiple antibiotic resistance) of *S. aureus* and *E. faecalis* were as susceptible as the standard strains. Although not active at the low concentrations cf current treatment drugs, there may be a potential use for Compound (1) as a treatment for multiply resistant staphylococci and enterococci not responding to the current drugs of choice.

Anaerobic Infections

Compound (1) is active against clinically significant anaerobes, *Clostridium perfringens, Clostridium difficile* and *Bacteroides fragilis. C. difficile* causes enterocolitis in hospitalized patients and is currently treated with vancomycin as the drug of choice. Induction of resistance is a potential problem with vancomycin. There could be a market for an oral drug for *C. difficile* enterocolitis as an alternative to vancomycin.

Anaerobic infections are generally mixed infections of one or more anaerobes with facultative bacteria, usually enteric Gram negative rods. The most common anaerobic pathogens are *Clostridium difficile* and *Bacteroides fragilis*. Current treatment with metronidazole in combination with other antibacterial drugs is generally efficacious. Given Compound (1)'s broad spectrum against both aerobic and anaerobic bacteria this could possibly treat these infections.

Enteric Infections

Compound (1) is very active against *Campylobacter jejuni*. *Campylobacter* is currently the greatest cause of enteric infections worldwide and is often treated because of its severity in some patients and the tendency for infection to predispose to development of Guillain-Barre syndrome, a serious CNS disease.

The relative resistance of enteric Gram negative bacteria could be a function of solubility and ability of Compound (1) to penetrate cells. The successful treatment of recalcitrant enteric infections and the successful treatment of *Salmonella* infection in animals has been shown.

Vulvo-Vaginitis

Compound (1) is active against *Neisseria gonorrhoeae*. Vulvo-vaginitis is caused by *Candida albicans, N. gonorrhoeae, Chlamydia trachomatis* and *Trichomonas vaginalis* (singly, not as co-infections). Compound (1) is active against two of these agents.

Formulating Compound (1) for greater solubility (and therefore probably greater absorption) could improve both its activity and its distribution in vivo.

TABLE 9

MIC/MBC (μg/mL) for Compound (1), ciprofloxacin and chlorhexidine against a range of bacteria of clinical significance

| Bacterial strain | Compound (1) MIC | Compound (1) MMC | Ciprofloxacin MIC | Ciprofloxacin MMC | Chlorhexidine MIC | Chlorhexidine MMC |
|---|---|---|---|---|---|---|
| Gram positive | | | | | | |
| Staphylococcus aureus ATCC 29213 | 16 | 16 | 0.25 | 0.25 | 2 | 8 |
| S. aureus - clinical isolate 1 | 16 | 16 | | | | |
| S. aureus - clinical isolate 2 | 16 | 16 | | | | |
| Enterococcus faecalis ATCC 29212 | 32 | 32 | 0.5 | 0.5 | | |
| E. faecalis - clinical isolate 1 | 32 | 32 | 1 | 1 | | |
| E. faecalis - clinical isolate 2 | 32 | 32 | | | | |
| Streptococcus pyogenes | 16.8 | 16.8 | | | | |
| Streptococcus pneumoniae ATCC49619 | 16 | 32 | | | | |
| Bacillus subtilis RMIT | 16 | 16 | | | | |
| Corynebacterium xerosis RMIT | 32.16 | 32.16 | | | | |
| Clostridium perfringens (48 h) | 16 | 32 | | | | |
| Clostridium difficile | 4 | | | | | |
| Gram negative | | | | | | |
| Moraxella catarrhalis RMIT | 32 | 32 | | | | |
| Neisseria gonorrhoeae WHO Strain VII | 2 | 2 | | | | |
| Haemophilus influenzae | 0.125 | 0.125 | 0.006 | 0.006 | | |
| Bacteroides fragilis (48 h) | 16 | 32 | | | | |
| Campylobacter spp. (48 h) | 128 | 128 | | | | |
| Campylobacter jejuni RMIT FF3 (48 h) | 2 | 2 | | | | |
| Acinetobacter calcoaceticus RMIT | 128 | 256 | | | | |
| Proteus vulgaris RMIT | 128 | 256 | | | 6 | 128 |
| Proteus mirabilis | 256 | >512 | | | | |
| Klebsiella oxytoca | 128 | 256 | | | | |
| Klebsiella pneumoniae | 512 | >512 | | | | |
| Salmonella Typhimurium | 256 | >512 | | | | |
| Escherichia coli ATCC 25922 | >512 | >512 | 0.02 | 0.02 | 2 | 4 |
| Pseudomonas aeruginosa ATCC 27853 | >512 | >512 | 0.25 | 0.25 | 32 | 64 |
| Serratia marcescens RMIT | >512 | >512 | | | 16 | 32 |
| Enterobacter aerogenes | 512 | 512 | | | | |

Example 15

Antifungal Activity of Compound (1)

NCCLS-USA Broth macrodilution method (RPMI medium).

Inoculum ~5×10$^4$ hyphal fragments/mL (haemocytometer). Miconazole control.

Minimum inhibitory concentration (MIC) and minimum fungicidal concentration (MFC 2 log reduction–99% kill) at 30° C., aerobically, 2, 7 and 10 days for yeasts and 4, 7 or 14 days for filamentous fungi.

Results are shown in Table 10.
Summary of Results

Compound (1) is fungicidal at relatively low concentrations against a broad range of clinically significant yeasts and filamentous fungi (Table 10).
Dermatophyte Infections Compound (1) shows good activity against 3 major causes of skin, hair and nail infections in humans and animals. Superficial fungal infections are the most common fungal infections worldwide. Treatment is prolonged, over months (and years for nail infections). Superficial treatments with antifungal lotions and creams is only partially effective. Current treatments, although generally low cost, have poor efficacy and frequent relapse rates. Oral systemic agents (terbinafine and itraconazole) are preferred for superficial infections in compromised patients and nail infections.
Systemic Infections Serious fungal infections in compromised patients have increased worldwide in prevalence and severity. Fungal infections are generally long term with a high therapeutic failure rate, frequent relapse and development of resistance by fungi. Candidiasis (*Candida albicans*) and aspergillosis (*Aspergillus fumigatus*) are the major fungal infections. Severe, invasive infections have a high mortality rate. Very few effective drugs are available (cf antibacterial drugs). Long term therapy makes safety and failure to induce resistance important considerations. Amphotericin B is the main drug of choice for many serious mycoses. It is fungicidal, with poor solubility and low bioavailability and is limited by toxicity and delivery problems and high therapy failure. The azoles and triazoles are fungistatic drugs (eg fluconazole and itraconazole) which have low toxicity, good pharmacokinetic characteristics but are often ineffective due to development of resistance on long term therapy.

Compound (1) has a broad spectrum, is fungicidal and has failed to induce resistance in *C. albicans* and *A. fumigatus* (see below).

TABLE 10

MIC/MFC (μg/mL) for Compound (1) and miconazole against clinically significant fungi

| Fungi | Compound (1) MIC | Compound (1) MMC | Miconazole MIC | Miconazole MMC |
|---|---|---|---|---|
| Dermatophytes (7 day) | | | | |
| Trichophyton rubrum | 1 | 256 | 1 | 64 |
| Epidermophyton floccosum | 0.5 | 16 | 0.25 | 0.25 |
| Microsporum gypseum | 1 | 8 | 4 | 64 |

TABLE 10-continued

MIC/MFC (μg/mL) for Compound (1) and miconazole against clinically significant fungi

| Fungi | Compound (1) | | Miconazole | |
|---|---|---|---|---|
| | MIC | MMC | MIC | MMC |
| Yeasts (4 day) | | | | |
| Candida albicans | 8 | 8 | 4 | 8 |
| Rhodotorula rubra | 8 | 8 | 8 | 32 |
| Filamentous fungi (7 day) | | | | |
| Fusarium graminearum | 4 | 8 | 32 | 32 |
| Rhizopus stolonifer | 4 | 16 | | |
| Aspergillus fumigatus | 8 | 32 | | |
| Penicillium chrysogenum | 1 | 2 | | |

Example 16

Sporicidal Activity of Compound (1)

*Bacillus subtilis* Endospores

*Aspergillus fumigatus* Asexual Exospores

Compound (1) in water+Tween 20 was tested for sporicidal activity up to 24 hours.

Compound (1) 512 μg/mL did not kill *B. subtilis* endospores in 24 hours.

Compound (1) 512 μg/mL killed *A. fumigatus* exospores at 24 hours but not 6 hours.

Inhalation of *Aspergillus* spores is the major mechanism of transmission. Activity against spores could be significant in prophylaxis of compromised individuals. Since the spore must germinate to infect, however, ultimately it is activity against vegetative forms of fungi that determine efficacy.

Example 17

Development of Resistance of Compound (1)

Bacterial and fungal strains were exposed to Compound (1) in sub-inhibitory concentrations continuously for 12 weeks and monitored for a rise in MIC indicating development of resistance mechanisms. A heavy and variable inoculum is used for weekly subculture so inhibitory concentrations each week vary. The standardized MIC is measured at the beginning and end of exposure. A greater than 4-fold variation of standardized MIC is indicative of increased resistance, or a rising trend in weekly MIC. The genera selected are known to develop resistance readily to many antibiotics and to be a major clinical problem.

Bacterial species and *C. albicans*, known to develop resistance to many current drugs, did not develop resistance to Compound (1) after 12 weeks continuous exposure (Table 11). Strains were scanned for abnormal microscopic and macroscopic changes. *Proteus vulgaris* lost the ability to swarm, indicating an effect on flagella. Other strains appeared normal. Tests are not yet complete for *R. rubra* and 3 moulds. Failure to induce the development of resistance in these strains is a significant attribute of Compound (1).

TABLE 11

Increase in MIC (μg/mL) of bacterial and fungal strains after 12 weeks continuous exposure to sub-inhibitory concentrations of Compound (1) in MHB

| | Standard MIC μg/mL | | 7 day MIC μg/mL no rising trend |
|---|---|---|---|
| Test strains | Initial | Final | Range to Week 12 |
| *Staphylococcus aureus* (MRSA clin isolate) | 16 | 16 | 32-128 |
| *Enterococcus faecalis* (MR clin isolate) | 32 | 32 | 64-128 |
| *Klebsiella oxytoca* | 128 | 256 | 256-512 |
| *Proteus vulgaris* | 128 | 128 | 64-256 |
| *Candida albicans* | 4 | 4 | 16-64 |
| *Rhodotorula rubra* | 8 | | 8-32 to Wk 5 |
| *Aspergillus fumigatus* | 8 | | 8-32 to Wk 5 |
| *Rhizopus stolonifer* | 4 | | 4-32 to Wk 5 |
| *Fusarium graminearum* | 4 | | 4-16 to Wk 5 |

Example 18

Antibacterial Activity of Compound (1) in the Presence of Blood

The activity of Compound (1) and ciprofloxacin was determined in the presence of plasma and whole blood (horse), by macrodilution method in Mueller Hinton broth to 48 h.

Compound (1) appeared to be relatively unaffected by the presence of 10% plasma and to be more active in the presence of 5% whole blood. The slightly improved inhibitory activity of drugs in the presence of blood sometimes occurs with antibacterial agents and is probably due to natural antibacterial factors present in blood. Further increasing the concentration of plasma and blood reduced the bactericidal activity of Compound (1) against *S. aureus* as shown in Table 13. Ciprofloxacin showed respectively a 4-fold and 2-fold decrease in activity against *S aureus* in the presence of 10% plasma and whole blood.

TABLE 12

Activity of Compound (1) in the presence of human whole blood and plasma

| | μg/mL | | | | |
|---|---|---|---|---|---|
| | — | 10% plasma | | 5% blood | |
| | MIC | MIC | MMC | MIC | MMC |
| *S. aureus* | 16 | 16 | 256 | 16 | 256 |
| *B. subtilis* | 16 | 8 | 8 | 8 | 16 |
| *A. calcoaceticus* | 128 | 128 | 128 | 64 | 256 |
| *M. catarrhalis* | 32 | 8 | 8 | 4 | 8 |

Example 19

Compound (1) Binding to Plasma Proteins

The MIC of Compound (1) was determined in increasing concentrations of plasma. Compound (1) has been shown to bind to human serum albumin and to agarose. Serum binding is significant in drug distribution and bioavailability.

The MIC of Compound (1) is significantly increased with increasing plasma concentrations. Bactericidal activity is much more affected than inhibitory activity.

Bioavailability of Compound (1) is significantly decreased in the presence of plasma proteins (Table 13). Compound (1) is reversibly bound to proteins.

TABLE 13

MIC/MMC (µg/mL) for Compound (1) in MHB in the presence of increasing concentrations of plasma

| % plasma in MHB | S. aureus MIC | Streptococcus pyogenes MIC |
|---|---|---|
| 0 | 4 | 4 |
| 1 | 4 | 4 |
| 2.5 | 8 | 8 |
| 5 | 8 | 8 |
| 10 | 16 | 16 |
| 20 | 32 | 32 |
| 50 | 128 | 64 |
| 100 | 128 | 256 |

Example 20

Rate of Kill

Test strains were inoculated into Compound (1) solutions in water and sampled immediately and at 1, 2, 4, 6 and 9 hours. Survivors were estimated by viable counts on MHA (35° C., 48 h).

Measure of kill: reduction in viable count (log) expressed as log reduction factors.

(e.g., a 1 log reduction=90% kill, 2 log=99% kill, 3 log=99.99% kill etc.)

Compound (1) showed rapid kill only against *Candida albicans*, with greater than a 99.999% reduction within 2 hours at 512 µg/mL and within 4 hours at 256 µg/mL as shown in FIG. 1.

Rate of kill was much slower against bacteria. The kill rate at 512 µg/mL was 99.99% within 2 hours for *B. subtilis* and 99.99% within 9 hours for *S. aureus*.

Ciprofloxacin was not tested.

TABLE 14

Log reduction factors for Compound (1) over 6 or 9 hours

| | Log reduction in viable count at time (h) Compound (1) µg/mL | | |
|---|---|---|---|
| | 512 | 256 | 128 |
| *Staphylococcus aureus* | 4 in 9 h | 0.5 in 6 h | |
| *Enterococcus faecalis* | 0.6 at 9 h | | |
| *Bacillus subtilis* | 4 in 2 h | 3.8 in 2 h | |
| *Klebsiella oxytoca* | 0 | 0 | |
| *Proteus vulgaris* | 1 in 6 h | 0.5 in 6 h | |
| *Acinetobacter calcoaceticus* | 1 in 6 h | 1 in 6 h | |
| *Candida albicans* | 5.5 at 2 h | 6 in 4 h | 2 in 6 h |

Example 21

Dosing Range Test of Compound (1) in Rat

The aim of this example was to establish absorption and blood levels of Compound (1) in the rat after a single dose oral administration.

Test Protocol

Sprague-Dawley rats (6 w/o, delivered 30 Jan. 2001) were acclimatised for 6 days in the Animal Facility under standardized environmental conditions (22° C.±3° C., rel hum 30-70%, artificial light, 12 h light/12 h dark). Rats were fed a conventional laboratory diet with food and water ad lib and caged 5 rats per cage.

Test Substance

Compound (1) was prepared as an aqueous suspension in sterile LPW. At higher concentrations the suspension was sonicated to reduce particle size sufficiently to pass through the gavage needle.

Compound (1) was tested at 1250, 1000, 500 and 100 mg/kg.

Test Method

Rats were randomly assigned to treatment groups, identified by numbering on tails. Doses were tested sequentially from the lowest dose.

| Group | A | 100 mg/kg | 5 Feb. 2001 |
|---|---|---|---|
| | B | 500 | 8 Feb. 2001 (not fasted) |
| | C | 500 | 12 Feb. 2001 (fasted) |
| | D | 1000 | 14 Feb. 2001 |
| | E | 1250 | 21 Feb. 2001 |

Compound (1) suspensions and the water control were administered at approx 100 mL/kgbw, in a single. One control and five treatment rats were weighed immediately before each dose administration, the dose volume calculated and the dose delivered by gavage (22 gauge stainless steel, smooth-balled end attached to a syringe).

Approximately 100-200 µl of blood (microfuge tube) was removed from the tail at 4 and 8 hours. Tails were prewarmed using a heat lamp and snipped at the tip with a large scalpel. Blood was massaged into a microfuge tube. Twenty four hour blood samples were not attempted because of the difficulty of snipping scarred tails and the distress caused to rats.

Blood was allowed to clot, centrifuged in a microfuge for 3 minutes (speed 14) and the serum separated and stored at −20° C.

Animals were observed twice daily for 7 days and all observations recorded individually for each animal. Animals were not weighed after the initial weighing. Sacrifice and necropsy was performed at 7 days.

Animals were euthanized by carbon dioxide.

Gross pathology was recorded and samples of heart, lung, liver, kidney, stomach, spleen, duodenum and colon removed (10% formalin) for histology.

Example 22

Blood Levels of Compound (1)

Bioassays

Bioassay for Compound (1) levels in blood was not possible because of the interference due to strong binding of Compound (1) to blood proteins and to agar.

Agar Diffusion

An agar diffusion assay for Compound (1) was not possible because Compound (1) bound so strongly to agar that no zones of inhibition were produced at any concentration from 1 to 512 µg/mL with susceptible strains of *S. aureus* or *Streptococcus pyogenes*. Both well diffusion and disk diffusion assays were attempted.

Broth Dilution

Dilution of serum in MHB and testing with a low inoculum of *S. pyogenes* (inhibited at 1 µg/mL of Compound (1) in MHB) was not possible because strong binding to plasma at high concentrations caused a significant prozone.

Assay by UV Spectroscopy

There was insufficient serum for assay of individual rat samples.

Samples for treatment groups and for controls were thus pooled and a mean level of Compound (1) for each treatment group determined.

Test Method

Compound (1) was extracted (×2) from serum by toluene and absorbance measured at 370 nm (Hitachi U2000). A spiked control using 100 µg/mL Compound (1) in 50% methanol/water (V/V) and untreated controls were also assayed.

Blood Levels

Absorption of Compound (1) from the gastrointestinal tract is very low, approximately 2% of the oral dose reaching the blood. Blood levels increased with dose level. Eight-hour levels were generally higher than 4-hour levels. The small difference between 4 and 8 hour levels suggests a slow absorption.

TABLE 15

| Compound (1) dose (mg/kg) | Sample time (hours) | Blood level of Compound (1) µg/mL Mean |
|---|---|---|
| 500 fed | 4 | 8 |
|  | 8 | 17 |
| 500 fasted | 4 | 12 |
|  | 8 | 14 |
| 1000 fasted | 4 | 26 |
|  | 8 | 21 |
| 1250 | 4 + 8 h | 27 |

Example 23

Antimicrobial Activity Spectrum of Compound (1)

Antifungal Activity
Filamentous Fungi

NCCLS-USA Broth Macrodilution method (RPMI medium)—draft. Inoculum 1–4×10$^5$ cfu. Miconazole control. This test was used for initial activity spectrum evaluations.

The MIC and MFC of filamentous fungi tested previously with the NCCLS-USA Broth Macrodilution Method were repeated using the new proposed standard microdilution method for testing fungi M38-P NCCLS-USA.

Results are of 2 or 3 replicates on different days.

Results were not significantly different from results obtained with the older method for all fungi previously tested. Amphotericin B was substituted for Miconazole as control for some tests.

Yeasts

NCCLS-M27-A Method for broth macro dilution antifungal susceptibility testing of yeasts; approved standard.

M38-P microdilution method for filmentous fungi also used.

Minimum inhibitory concentration (MIC) and minimum fungicidal concentration (MFC—2 log reduction—99% kill) at 35° C., 48 hours. Results of 2 or 3 replicates on different days for each method. Results were not significantly different for the two methods. M38P only reported for yeasts and filamentous fungi.

TABLE 16

MIC/MFC (µg/mL) for Compound (1) and Amphotericin B against clinically significant fungi - M38 - P method

|  | Compound (1) | | Amphotericin B | | Miconazole | |
|---|---|---|---|---|---|---|
|  | MIC | MMC | MIC | MMC | MIC | MMC |
| Yeasts (24 h, 35° C.) | | | | | | |
| Candida albicans | 8 | 8 | 0.25$_1$ | 0.25 | | |
| C. guillermondii RMIT 176 | 2 | 2 | 0.03 | 0.06 | 1 | 1 |
| C. krusei RMIT 177 | 4 | 4 | 0.5$_2$ | 0.5 | 2 | 2 |
| C. parapsilosis RMIT 178 | 2 | 2 | 0.25$_3$ | 0.25 | 0.5 | 0.5 |
| C. tropicalis RMIT 181 | 4 | 4 | 0.25 | 0.5 | 1 | 2 |
| C. glabrate RMIT 157 | 2 | 2 | 0.5 | 1 | 0.25 | 0.5 |
| Cryptococcus neoformans | 1 | | 0.5 | | 4 | |
| Filamentous fungi (48 h, 35° C.) | | | | | | |
| Aspergillus fumigatus | 8 | 32 | 1 | 8 | | |
| A. niger | 8 | 16 | 2 | 2 | | |
| A. flavus | 16 | 32 | 8 | 8 | | |
| Fusarium graminearum | 4 | 8 | 4 | 8 | | |
| F. chlamydosporum | 8 | 8 | 2 | 2 | | |
| Rhizopus stolonifer | 4 | 16 | >16 | | | |
| R. oryzae | 64 | 64 | 4 | 4 | | |
| Rhizomucor pusillus | 4 | 8 | 1 | 1 | | |
| Paecilomyces variotii | 1 | 2 | 1 | 1 | | |
| Dematiaceous fungi | | | | | | |
| Fonsecaea pedrosoi | 2 | 2 | 8 | 16 | | |
| Phialophora verrucosa | 16 | 32 | 2 | 4 | | |
| Pseudoallescheria boydii | 2 | 4 | 4 | 16 | | |
| Dermatophytes | | | | | | |
| Trichophyton rubrum | 1 | 256 | | | | |
| Epidermophyton floccosum | 0.5 | 16 | | | | |
| Microsporum gypseum | 1 | 8 | | | | |

Permitted range for Amphotericin B control
0.25-1 µg/mL.
0.5-2.0 µg/mL
0.25-1 µg/mL Bacteria Methods NCCLS-M7-A5 Standard Method—Broth microdilution (Mueller-Hinton). Inoculum 1–4×10$^4$ cfu. Ciprofloxacin test control. Chlorhexidine and cetyl trimethyl ammonium bromide (CTAB) for disinfectant and antiseptic activity comparison.

NCCLS-M7-A5 Standard Method—macrodilution (Mueller Hinton±specified enrichments) was also used. Minimum inhibitory concentration (MIC) and minimum bactericidal concentration (MBC) as 3 log reduction (99.9% kill) at 35° C., 24 hours, aerobically. 48 h titres were not significantly different and are not reported.

Micro and macro dilution methods did not give significantly different MIC/MMC.

TABLE 17

All tests performed as 2 or 3 replicates on different days.

| | Compound (1) µg/mL | | Ciprofloxacin | | Chlorhexidine | | CTAB | |
|---|---|---|---|---|---|---|---|---|
| Bacterial strain | MIC | MMC | MIC | MMC | MIC | MMC | MIC | MMC |
| Gram positive | | | | | | | | |
| Staphylococcus aureus ATCC 29213 | 16 | 16 | 0.25 | 0.25 | 2 | 8 | 16 | 32 |
| S. aureus - clinical isolate 1 | 16 | 16 | | | | | | |
| S. aureus - clinical isolate 2 | 16 | 16 | | | | | | |
| Enterococcus faecalis ATCC 29212 | 32 | 32 | 0.5 | 0.5 | | | | |
| E. faecalis - clinical isolate 1 | 32 | 32 | | | | | | |
| E. faecalis - clinical isolate 2 | 32 | 32 | | | | | | |
| Streptococcus pyogenes RMIT | 16 | 16 | | | | | | |
| Streptococcus pneumoniae | 2 | 2 | | | | | | |
| Bacillus subtilis RMIT | 16 | 16 | | | | | | |
| Corynebacterium xerosis RMIT | 32 | 32 | | | | | | |
| Gram negative | | | | | | | | |
| Moraxella catarrhalis RMIT | 32 | 32 | | | | | | |
| Neisseria gonorrhoeae | 2 | 2 | | | | | | |
| Haemophilus influenzae | 0.125 | 0.125 | | | | | | |
| Acinetobacter calcoaceticus RMIT | 128 | 256 | | | | | | |
| Proteus vulgaris RMIT | 128 | 128 | | | 6 | 128 | 128 | 256 |
| Proteus mirabilis | 256 | >512 | | | | | | |
| Enterobacter aerogenes | 512 | 512 | | | | | | |
| Klebsiella oxytoca | 128 | 256 | | | | | | |
| Klebsiella pneumoniae | 512 | >512 | | | | | | |
| Escherichia coli ATCC 25922 | >512 | >512 | 0.02 | 0.02 | 2 | 4 | 16 | 16 |
| Pseudomonas aeruginosa ATCC 27853 | >512 | >512 | 0.25 | 0.25 | 32 | 64 | 512 | >512 |
| Serratia marcescens RMIT | >512 | >512 | | | 16 | 32 | 128 | 128 |
| Bacteroides fragilis | 16 | 32 | | | | | | |

Campylobacter

Compound (1) was tested against a range of clinical strains of *Campylobacter* spp. isolated from humans.

TABLE 18

MIC/MMC (µg/mL) of Compound (1) by NCCLS - M7 A5 macro dilution test, 42° C., 48 h, microaerophilic incubation

| | MIC | MMC |
|---|---|---|
| Campylobacter jejuni 54/1-2 | 2 | 2 |
| C. jejuni 541-3 | 2 | 2 |
| C. coli 54/2 | 4 | 4 |
| C. foetus 54/3 | 2 | 2 |
| C. hyointestinalis 54/4 | 2 | 2 |
| C. sputorium 54/5 | 2 | 2 |
| C. laniolis 54/6 | 2 | 2 |

*Campylobacter* is the most common cause of gastroenteritis infection worldwide (bloody diarrhoea, abdominal pain, vomiting, headache, fever, lasting about 1 week). Sequelae are arthritis and Guillain-Barre syndrome (0.1%). It is acquired mainly from eating poultry. Incidence is about 2.5 million persons/year in USA. *C. jejuni* accounts for 99% of cases. It can vary from sub-clinical to severe in compromised patients. It is usually untreated with only fluid replacement or, if the disease is severe or threatening, with antibiotics (Erythromycin, tetracycline or fluoroquinolone).

TABLE 19

MIC/MFC (µg/mL) for Compound (1) (24 h, 35° C., $O_2$ - micro method)

| Bacteria | MIC | MMC |
|---|---|---|
| Neisseria gonorrhoeae | 2 | 2 |
| Haemophilus influenzae | 0.125 | 0.125 |
| Streptococcus pneumoniae | 2 | 2 |

The above are significant human pathogens, all of which have successful treatment regimens with antibiotics. *N. gonorrhoeae* is a cause of vaginitis in women. Compound (1) is thus active at low concentrations against two causes, *Candida albicans* and *N. gonorrhoeae*.

Trichomonas vaginalis
Method

The MIC of clinical isolate of *Trichomonas vaginalis* was determined by macrobroth dilution in Diamond's complete medium, modified by Klass (Modified TYM) as described by Garcia, L. Cultures were contained in 5 mL glass, screw-capped bottles without air-spaces. Volumes of 5 mL of log 2 dilutions, from 512 µg/mL Compound (1) in 5% DMSO to 0.25 µg/mL Compound (1) in 0.002% DMSO in modified TYM, were inoculated with 0.5 mL volume of cells in log phase of growth giving a final inoculum density of $1 \times 10^4$ to $3 \times 10^4$ cell/mL. Bottles were incubated aerobically at 37° C. for 24 h before microscopic examination of motility. MIC was determined as the lowest concentration showing no motility. Aliquots of 0.5 mL from all tubes showing no motility were subcultured into further 5 mL volumes of modified TYM and incubated aerobically at 37° C. for up to 5 days to confirm non-viability.

Tests were validated by growth controls in TYM, modified TYM with 2.5% DMSO and modified TYM with 5% DMSO.

Tests were performed as 3 replicates on different days.

Results

|  | MIC | MMC |
|---|---|---|
| Trichomonas vaginalis | 4 µg/mL | 4 µg/mL |

Example 24

Development of Resistance to Compound (1)

Selected resistant strains from the 12 week resistance testing were retested simultaneously with parent strains using the new microdilution method.

TABLE 20

Change in MIC (µg/mL) of fungal strains after 12 weeks continuous exposure to sub-inhibitory concentrations of Compound (1) in MHB

| | MIC µg/mL M38-P | |
|---|---|---|
| Test strains | Initial | Final |
| Rhodotorula rubra | 8 | 16 |
| Aspergillus fumigatus | 8 | 8 |
| Rhizopus stolonifer | 4 | 16 |
| Fusarium graminearum | 4 | 4 |

Fungi exhibit up to a four-fold difference in MIC on repeat testing. Significant increases in MIC are ≥8-fold.

There is no significant development of resistance by the filamentous mould strains tested.

Example 25

Effect of Formulation in Ethanol on Activity

The effect of formulation in DMSO and ethanol on the MIC of Compound (1) was compared for *Candida albicans*, *Salmonella Typhimurium* and *Escherichia coli* using both the macrodilution and microdilution tests.

Stock solutions in ethanol were allowed to stand for 48 h before use to improve solubility. Compound (1) is not as soluble in ethanol as in DMSO. The concentration of ethanol and DMSO was kept constant at 2% and compared to a decreasing concentration of solvent on normal dilution of the stock solution. There was no difference between the two test methods. There was no difference in MIC between constant and decreasing levels of DMSO. Only *E. coli* showed an enhanced susceptibility to ethanol in the presence of a constant 2% ethanol.

TABLE 21

Effect of solvent on MIC (µg/mL) of Compound (1) using microdilution

| | DMSO | | EtOH (2%) | |
|---|---|---|---|---|
| | MIC | MBC | MIC | MBC |
| Escherichia coli | 512 | >512 | 128 | 256 |
| Salmonella Typhimurium | 512 | >512 | 512 | >512 |
| Candida albicans | 8 | 16 | 8 | 16 |

The synergistic effect of ethanol on. *E. coli* was noted previously when solvents were being tested for selection of an appropriate solvent for the drug. Ethanol has no enhancing effect on *Staphylococcus, Salmonella* or *Candida*. DMSO is a better solvent for the drug in in-vitro tests. Ethanol will be used for animal studies.

Example 26

Stability of Compound (1) Solutions on Storage

Stock solutions of Compound (1) at 512 µg/mL in water+ 5% DMSO were stored at room temperature (RT~18-21° C.), 4° C. and −20° C. for up to 12 weeks and the potency tested by measurement of MIC for *Bacillus subtilis* at 2-weekly intervals.

TABLE 22

Stability of Compound (1) stock solutions at 512 µg/mL tested by measurement of the MIC/MBC for *Bacillus subtilis* (24 h, 35° C.) at 2 weekly intervals

| | RT[1] | | 4° C. | | −20° C.[2] | |
|---|---|---|---|---|---|---|
| Test time | MIC | MBC | MIC | MBC | MIC | MBC |
| 0 | 4 | 8 | 4 | 8 | 4 | 8 |
| 2 | 4 | 8 | 4 | 8 | 4 | 8 |
| 4 | 4 | 8 | 4 | 16 | 4 | 16 |
| 6 | 4 | 16 | 4 | 16 | 4 | 16 |
| 8 | 8 | 16 | 4 | 16 | 4 | 16 |
| 10 | 8 | 16 | 4 | 16 | 4 | 16 |
| 12 | 8 | 16 | 4 | 16 | 4 | 16 |

[1]Solution changed from light yellow to dark yellow after 8 weeks.
[2]Solution changed from light yellow to dark yellow after 2 weeks.

Compound (1) is very stable, dilute solutions retaining potency for 12 weeks on storage at 4° C. and −20° C. Twofold loss of potency at room temperature after 6 weeks is very low compared to working solutions of antibiotics. It is also within the allowed variation range for MIC measurements for bacteria (2-fold). Control antifungals were not tested.

Example 27

Effect of Compound (1) on Growth of the Human Malaria Parasite, *Plasmodium falciparum*, in Human Red Blood Cells In Vitro The aim of this example was to quantify the effect of Compound (1) on invasion and growth of the human malaria parasite *Plasmodium falciparum* in human red blood cells in vitro.

Methods

Malaria Parasites

3D7 is a well characterised in vitro culture-adapted line of *P. falciparum* that was used for these experiments. The parasite undergoes repeating cycles of growth and replication within human red blood cells. The duration of each complete cycle is 48 hours, beginning with young ring-stage parasites which mature through pigmented trophozoites during the first 24 hours of the cycle to segmented schizonts which burst to release infectious merozoites which rapidly invade red blood cells. Newly invaded merozoites become ring forms, and the cycle continues.

Parasite Culture and Growth Inhibition Assays

*P. falciparum* parasites were maintained in synchronous in vitro culture in freshly collected human red blood cells, using well-established techniques. For invasion assays, red blood cells containing stage-synchronized mature, pigmented trophozoites were purified and resuspended in fresh human red blood cells, so that approximately two in every 100 red blood cells was parasitised (2% parasitaemia). Fresh culture media was added to give a final red blood cell concentration of $2\times10^8$ red cells/ml.

Aliquots of the red blood cell suspension containing either the test compound, the vehicle alone (in this case EtOH) or PBS (control) were incubated at 37° C. in an atmosphere of reduced oxygen tension (1% $O_2$, 3% $CO_2$, 96% $N_2$). Thin blood smears were made immediately (time=0) then subsequently after 24, 48 and 72 hours of culture. For each smear, parasitaemia and stage of parasite maturation was quantified by microscopic examination after staining with Giemsa at pH 7.2. This allowed invasion, parasite development and subsequent re-invasion to be quantified. At each sampling time point, the culture medium (±compound/vehicle) in all samples was completely replaced with fresh medium.

Compound (1) was tested as aqueous solutions of 100, 400 and 1000 µg/ml each containing 10% EtOH. Stock solutions were stored at 4° C. until required. For the assay, each solution was further diluted 1:40 in complete parasite culture medium (pH 7.2) to the desired working concentration (5, 10 and 25 µg/ml), then sterile filtered (0.22 µm) before being added to the parasitised red blood cell suspension. Stock solutions were stored at 4° C. throughout the duration of the assay, and diluted appropriately in parasite culture medium when required. It should be noted that at 1000 µg/ml, the compound was incompletely soluble, even after warming to 37° C. and vigorous vortexing. Thus the tests performed at a putative concentration of 25 µg/ml, may in fact have been performed at a lower effective concentration.

Results

Figure 2:
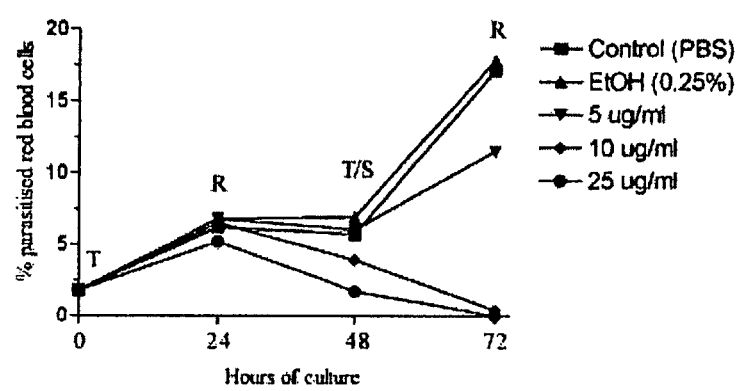
FIG. 2 is a graph of % parasitised blood cells vs hours of culture in Example 26 in which T=Trophozoites, R=Rings and T/S=Trophozoites or Schizonts.

The effect of Compound (1) on parasite growth was tested at final concentrations of 5, 10 and 25 µg/ml. Results are presented graphically in FIG. 2. A concentration-dependent inhibitory effect on parasite growth and replication was detected at all concentrations of drug tested, being greatest at the highest concentration tested (25 µg/ml) after 72 hours of culture. EtOH alone, at a final concentration of 0.25% had no significant effect on parasite growth. All concentrations of the compound tested showed no detectable adverse effect on red blood cell morphology.

At 25 µg/mL no parasites were observed and at 10 µg/mL only very few were found, suggesting that the compound actually killed the parasites.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Burton, H., Duffield, G., *J. Chem. Soc.*, 1949, 78
Denisenko P. P., Tarasenko A. A., Russian patent No. 2145215, "Substances having antimicrobial, antifungal, antiprotozoal activity" published 10 Feb. 2000
Foyer, G., *Chemistry of nitro and nitroso groups*, Moscow, 1973, Pt.2, pp. 194-195
Garcia, L., Parasite culture: *Trichomonas vaginalis, Clinical Microbiology Procedures Handbook*, H. D. Isenberg (ed.), volume 2, American Society for Microbiology, Washington, USA, 7.9.3.1-7.9.3.6.
Hamlin, K., Weston, A., *J. Am. Chem. Soc.* 71, 2210 (1949)
Knoevenagel, E., Walter, L., *Ber.*, 37, 4502 (1904)
Kuna P., Chemical radiation protection, Moscow, 1989, pp. 25-28
Mashkovskiy M. D., *Clinical agents, Pt.* 2, Moscow, 1986, p. 189
Perekalkin V. V., *Unlimited nitrocompounds*, Leningrad, 1982, pp. 55, 59, 61, 71, 73, 88, 89, 91, 95
Perekalkin V. V., *Unlimited nitrocompounds*, Leningrad, 1982, p. 67
Perekalkin V. V., *Unlimited nitrocompounds*, Moscow, 1966, p. 119
Vladimirov V. G. et al., *Radiation protectors, structure and operation*, Kiev, 1989, p. 139

The claims defining the invention are as follows:

1. A method for the therapeutic treatment of a skin or soft tissue infection wherein the infection is caused by an organism selected from the group consisting of *Enterococcus faecalis, Staphylococcus epidermidis, Clostridium perfringens, Proteus vulgaris, Proteus mirabilis, Streptococcus pyogenes, Candida albicans, Microsporum*, and *Epidermophyte*; the method comprising administering to an animal in need thereof an effective amount of a compound of general formula I:

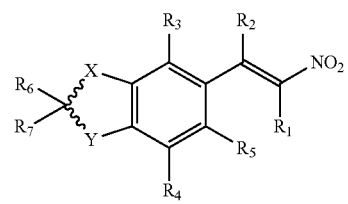

in which
X and V are O;

⸺ is a double or single bond depending on the heteroatoms X and Y;
$R_1$ to $R_5$ are either the same or different, and are each hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, arylthio, acylthio, or a phosphorus-containing group; and
$R_6$ and $R_7$ are either the same or different, and are each hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, arylthio, acylthio, or a phosphorus-containing compound; or one of $R_6$ and $R_7$ is absent when there is a double bond present, or a pharmaceutically-acceptable salt thereof.

2. The method of claim 1, wherein $R_1$ and $R_2$ are either the same or different, and are each hydrogen, hydroxy, halogen, or optionally-substituted $C_{1-6}$ alkyl.

3. The method of claim 1, wherein $R_3$ to $R_5$ are either the same or different, and are each hydrogen, hydroxy, halogen, nitro, $C_{1-6}$ alkoxy, or optionally-substituted $C_{1-6}$ alkyl.

4. The method as claimed in claim 1, in which X, Y, $\xi$, $R_6$ and $R_7$ are each as defined in claim 1; $R_1$ and $R_2$ are either the same or different, and are each hydrogen, hydroxy, Cl, Br, or $C_{1-4}$ alkyl; and $R_3$ to $R_5$ are either the same or different, and are each hydrogen, hydroxy, Cl, Br, nitro, $C_{1-4}$ alkoxy or $C_{1-4}$ alkyl.

5. The method of claim 1, wherein the compound is 3,4-methylenedioxy-β-methyl-β-nitrostyrene.

6. The method of claim 1, wherein the compound is 3,4-methylenedioxy-β-nitrostyrene.

7. The method of claim 1, wherein the animal is a human.

* * * * *